United States Patent
Naasani

(10) Patent No.: US 7,198,847 B2
(45) Date of Patent: *Apr. 3, 2007

(54) NANOCRYSTALS

(75) Inventor: Imad Naasani, Columbus, OH (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/952,701

(22) Filed: Sep. 29, 2004

(65) Prior Publication Data

US 2005/0112376 A1    May 26, 2005

(51) Int. Cl.
 *B32B 5/16* (2006.01)

(52) U.S. Cl. .................. 428/403; 428/407; 428/690; 252/301.4 R; 252/301.4 S; 252/301.6 R; 252/301.6 S

(58) Field of Classification Search ............ 428/403, 428/407, 630; 252/301.4 R, 301.4 S, 301.6 R, 252/301.6 S
See application file for complete search history.

(56) References Cited

U.S. PATENT DOCUMENTS

| | | |
|---|---|---|
| 4,642,334 A | 2/1987 | Moore et al. |
| 4,946,778 A | 8/1990 | Ladner et al. |
| 5,034,506 A | 7/1991 | Summerton et al. |
| 5,151,507 A | 9/1992 | Hobbs, Jr. et al. |
| 5,187,085 A | 2/1993 | Lee |
| 5,558,991 A | 9/1996 | Trainor |
| 5,596,086 A | 1/1997 | Matteucci et al. |
| 5,602,240 A | 2/1997 | De Mesmaeker et al. |
| 5,637,258 A | 6/1997 | Goldburt et al. |
| 5,679,785 A | 10/1997 | Engels et al. |
| 5,736,137 A | 4/1998 | Anderson et al. |
| 5,789,157 A | 8/1998 | Jensen et al. |
| 5,948,386 A | 9/1999 | Katti et al. |
| 5,969,135 A | 10/1999 | Ramasamy et al. |
| 5,990,479 A | 11/1999 | Weiss et al. |
| 6,114,038 A * | 9/2000 | Castro et al. ........ 428/402.24 |
| 6,179,912 B1 | 1/2001 | Barbera-Guillem et al. |
| 6,221,602 B1 | 4/2001 | Barbera-Guillem et al. |
| 6,261,779 B1 | 7/2001 | Barbera-Guillem et al. |
| 6,306,610 B1 * | 10/2001 | Bawendi et al. ............ 435/7.1 |
| 6,319,426 B1 * | 11/2001 | Bawendi et al. ...... 252/301.4 R |
| 6,326,144 B1 * | 12/2001 | Bawendi et al. ............... 435/6 |
| 6,855,551 B2 * | 2/2005 | Bawendi et al. ............... 436/6 |

* cited by examiner

*Primary Examiner*—Leszek Kiliman
(74) *Attorney, Agent, or Firm*—Pepper Hamilton LLP

(57) ABSTRACT

Provided herein are compositions of functionalized, fluorescent nanocrystals comprising fluorescent nanocrystals coated with an imidazole-containing compound; compositions of functionalized, fluorescent nanocrystals comprising fluorescent nanocrystals coated with an imidazole-containing compound and cross-linked with a phosphine cross-linking compound; compositions of functionalized fluorescent nanocrystals operably bound to molecular probe; a process of making functionalized, fluorescent nanocrystals; and a process of using functionalized, fluorescent nanocrystals in a detection system.

22 Claims, 8 Drawing Sheets

FIG. 7A
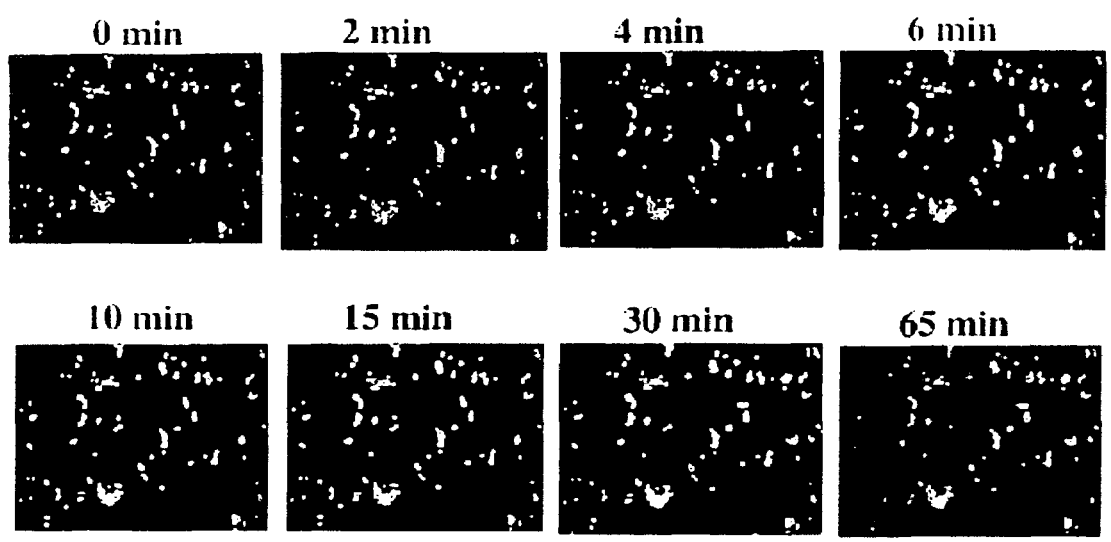
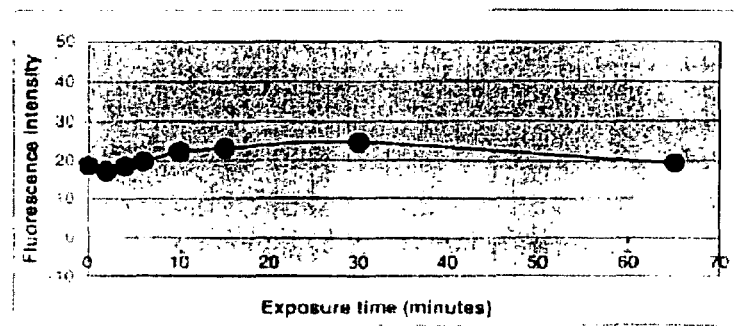
FIG. 7B

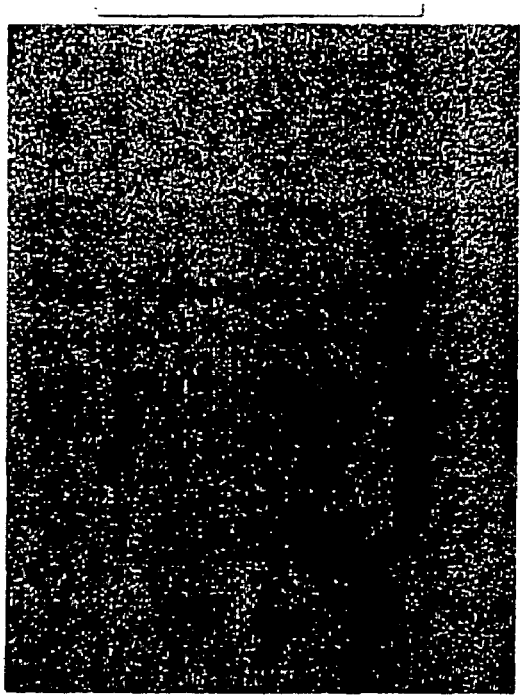 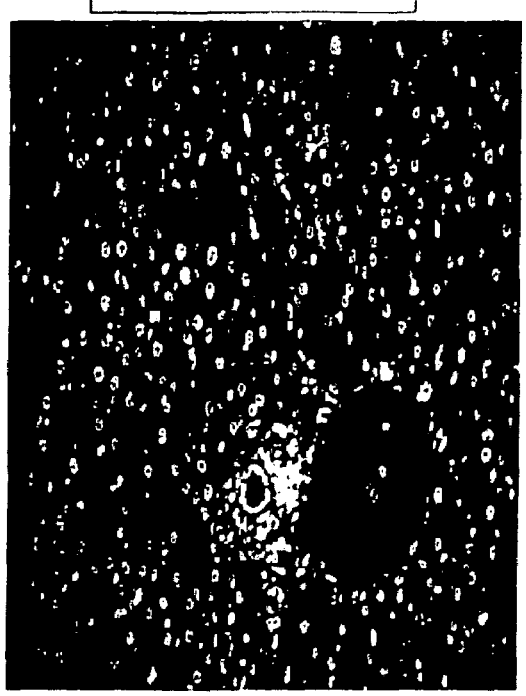
FIG 8A — Phase contrast
FIG. 8B — Fluorescence

NANOCRYSTALS

This invention was made, in part, with government support under contract DAAD17-01-C-0024 with the United States Army Research Laboratory. The government has certain rights in this invention.

CROSS-REFERENCE TO RELATED APPLICATIONS

This application claims the benefit of U.S. Provisional Application No. 60/322,982, filed Sep. 17, 2001, and U.S. Provisional Application No. 60/379,208, filed May 9, 2002, and U.S. Non-Provisional Patent Application No. 10/245,082 filed Sep. 17, 2002, titled "Nanocrystals" all of which are incorporated herein by reference.

BACKGROUND OF THE INVENTION

This invention relates to novel compositions comprising nanocrystals which are both functionalized and have enhanced fluorescent properties. More particularly, the present invention relates to coating nanocrystals with a compound which imparts to the coated nanocrystals properties which include water-solubility, functionalization, and an unexpected enhancement of fluorescence intensity.

Fluorescence-based analyses and nonisotopic detection systems have become a powerful tool and preferred mode in scientific research and clinical diagnostics, as well as in many industrial applications, for the detection of biomolecules using various assays including, but not limited to, flow cytometry, nucleic acid hybridization, DNA sequencing, nucleic acid amplification, immunoassays, histochemistry, and functional assays involving living cells. In particular, while fluorescent organic molecules such as fluorescein and phycoerythrin are used frequently in detection systems, there are disadvantages in using these molecules in combination. For example, photobleaching (fading of intensity under light sources) is a major problem that hinders the accuracy of quantitative measurements using these molecules. In addition, each type of fluorescent molecule typically requires excitation with photons of a different wavelength as compared to that required for another type of fluorescent molecule due to the relatively narrow absorption spectrum of each. Even when a single light source is used to provide a single excitation wavelength (in view of the spectral line width), there is often insufficient spectral spacing between the emission optima of different fluorescent molecules to permit individual and quantitative detection without substantial spectral overlap. That is, typical fluorescent dyes each have an emission spectrum that is rather broad which often limits combinations of fluorescent molecules that can be used simultaneously. Additionally, conventional fluorescent dyes have limited fluorescence intensity over time (suffer from photobleaching). Further, currently available nonisotopic detection systems typically are limited in sensitivity due to the finite number of nonisotopic molecules that can be used to label a target molecule to be detected.

Semiconductor nanocrystals are now being evaluated for their adaptation to detection systems in aqueous environments. An advantage of such nanocrystals is that they can be produced in a narrow size distribution and, since the spectral characteristics are a function of the size, can be excited to emit a discrete fluorescence peak of narrow bandwidth. In other words, the ability to control the spectral characteristics of nanocrystals (narrow bandwidth, discrete emission wavelengths, a single wavelength can excite an array of nanocrystals with different emissions) is the major attracting point in their use. Another advantage of the nanocrystals is their resistance toward photobleaching under intensive light sources. As known in the art, a manual batch method may be used to prepare semiconductor nanocrystals of relative monodispersity (e.g., the diameter of the core varying approximately 10% between quantum dots in the preparation), as has been described previously (Bawendi et al., 1993, J. Am. Chem. Soc. 115:8706). Advances in nanocrystal core production and reductions in average particle size have been achieved by a continuous flow process (U.S. Pat. No. 6,179,912, the disclosure of which is herein incorporated by reference). Additionally, semiconductor nanocrystals of different sizes may be excited with a single spectral wavelength of light.

Examples of semiconductor nanocrystals are known in the art to have a core selected from the group consisting of CdSe, CdS, CdTe (collectively referred to as "CdX")(see, e.g., Norris et at., 1996, Physical Review B. 53:16338–16346; Nirmal et al., 1996, Nature 383: 802–804; the disclosures of which are hereby incorporated by reference).

Core semiconductor nanocrystals, however, exhibit low fluorescence intensity upon excitation, and additionally, lack water-solubility. The low fluorescence intensity has been ascribed to the presence of surface energy states that act as traps which degrade the fluorescence properties of the core nanocrystal.

Efforts to improve the fluorescence intensity involve passivating (or capping) the outer surface of a core nanocrystal in thereby reducing or eliminating the surface energy states associated therewith. Organic molecules, such as tri-n-octyl phosphine (TOP) and tri-n-octyl phosphine oxide (TOPO) have been used for passivation. Inorganic materials have also been used for passivation; i.e., core nanocrystals have been passivated with an inorganic coating ("shell") uniformly deposited thereon. The shell which is typically used to passivate CdX core nanocrystals is preferably comprised of YZ wherein Y is Cd or Zn, and Z is S, or Se, or even Te. Semiconductor nanocrystals having a CdX core and a YZ shell have been described in the art (see, e.g., Danek et at., 1996, Chem. Mater. 8:173–179; Dabbousi et al., 1997, J. Phys. Chem. B 101:9463; Rodriguez-Viejo et al., 1997, Appl. Phys. Lett. 70:2132–2134; Peng et al., 1997, J. Am. Che. Soc. 119:7019–7029; the disclosures of which are hereby incorporated by reference). However, the above described passivated semiconductor nanocrystals have been reported to have limited improvements in fluorescence intensity (with reference to quantum yield), and to have solubility in organic, non-polar (or weakly polar) solvents only.

To make fluorescent nanocrystals useful in biological applications or detection systems utilizing an aqueous environment, it is desirable that the fluorescent nanocrystals used in the detection system ate water-soluble, "Water-soluble" is used herein to mean sufficiently soluble or suspendable in an aqueous-based solution, such as in water or water-based solutions or buffer solutions, including those used in biological or molecular detection systems as known by those skilled in the art. One method to impart water-solubility to semiconductor nanocrystals (e.g., CdX core/YZ shell nanocrystals) is to exchange the overcoating layer of TOP or TOPO with a coating, or "capping compound", which will impart some water-solubility. For example, a mercaptocarboxylic acid may be used as a capping compound to exchange with the organic layer (see, e.g., U.S. Pat. No.

6,114,038, the disclosure of which is herein incorporated by reference; see also, Chan and Nie, 1998, Science 281: 2016–2018). The thiol group of monothiol capping compound bonds with the Cd—S or Zn—S bonds (depending on the composition of the nanocrystal), creating a coating which is not easily displaced in solution, and imparting some stability to the nanocrystals in suspension. Further advances in water solubility, stability, and fluorescence properties have been achieved by using novel amino acid coating technology. In preferred embodiments, a diaminocarboxylic acid is either used to exchange with the capping compound, or is used to overlay the capping compound in operative connection therewith (see, e.g., U.S. Pat. No. 6,114,038). Successive amino acid layers may then be added.

Another method to make the CdX core/YZ shell nanocrystals water-soluble is by the formation of a coating of silica around the semiconductor nanocrystals (Bruchez, Jr. et al., 1998, Science 281:2013–2015; U.S. Pat. No. 5,990,479) utilizing a mercapto-based linker to link the glass to the semiconductor nanocrystals. An extensively polymerized polysilane shell has been reported to impart water solubility to nanocrystalline materials, as well as allowing further chemical modifications of the silica surface. However, depending on the nature of the coating compound, coated semiconductor nanocrystals that have been reported as water-soluble may have limited stability in an aqueous solution, particularly when exposed to air (oxygen) and/or light. For example, oxygen and light can cause mercapto-based monothiols used in coating or linking to become oxidized, thereby forming disulfides which destabilize the attachment of the coating or linking molecules to the nanocrystal. Thus, oxidation may cause the coating or linking molecules to migrate away from the outer surface of the nanocrystals, thereby exposing the surface of the nanocrystals resulting in "destabilized nanocrystals" Destabilized nanocrystals form aggregates when they interact together, and the formation of such aggregates eventually leads to irreversible flocculation of the nanocrystals. Additionally, current means for passivating semiconductor nanocrystals are still rather inefficient in increasing the fluorescence intensity to a level desired for detection systems (e.g., in providing a significant increase in sensitivity in fluorescence-based detection systems as compared to currently available fluorescent dyes).

Thus, there remains a need for a nanocrystal that overcomes the above-referenced limitations, and others.

SUMMARY OF THE INVENTION

An embodiment of the present invention provides compositions comprising functionalized, fluorescent nanocrystals for use in nonisotopic detection systems, methods of making the same, and methods of using the same. The functionalized, fluorescent nanocrystals according to this embodiment have several unique features. The functionalized, fluorescent nanocrystals avoid use of an organic solvent or mercapto-based compounds as a coating or linking agent such as for a passivation and/or as a capping compound. Such agents (e.g., TOPO, mercapto-based compounds, and the like) have several disadvantages that make use of such coated nanocrystals problematic in many biological applications. For example, such agents may be one or more of: sensitive to sulfhydryl-containing reagents, cytotoxic, and have a tendency to be chemically unstable (e.g., when stored or used in an environment where water-solubility is a desired function; or when exposed to oxygen and light). Further, applying a mercapto-based compound as a linker (U.S. Pat. No. 5,990,479) or coating system (U.S. Pat. No. 6,114,038) is an extra step that may be obviated in the process of producing fluorescent nanocrystals.

In accordance with another embodiment of the present invention, functionalized, fluorescent nanocrystals display an unexpected increase in fluorescence intensity as compared to other known semiconductor nanocrystal formulations. Mechanisms that increase fluorescence intensity, may include, but are not limited to, passivation, charge transfer, or a combination thereof.

The concept of passivation has been previously described herein. A coating comprising an imidazole-containing compound may passivate the outer surface of a core nanocrystal. Furthermore, a coating comprising an imidazole-containing compound cross-linked with a phosphine cross-linking compound may also stabilize and passivate the outer surface of a core nanocrystal. The stabilizing effect provided by the combined coating comprises protection of the crystals from degradative effects of acidic solutions or high ionic strength solutions. The passivating effect is due to the capping of surface Cd or Zn atoms or the like (e.g., other metal ions) by imidazole complexation, and to the capping of the counter atoms (Se or S or the like) by complexation with the phosphine cross-linking compounds.

As to charge dislocation, for example, imidazole and alkyl phosphine moieties, present in the coating comprising an imidazole containing compound, may be susceptible to excitation by a sufficient excitation light source. Such excitation may lead to charge transfer from the imidazole and/or phosphine moieties to the nanocrystal structure thereby resulting in an increase in fluorescence intensity, as compared to a fluorescence intensity without such internal charge transfer.

As for energy condensation and resonance, it is anticipated that the integration of the $\pi$ electrons in the imidazole and phosphine moieties with the excited electrons at the higher energy band of the core crystal is producing an energy condensation effect that yields, higher level of radiative relaxation. The nanocrystals are functionalized to be water-soluble and to contain one or more reactive functionalities to which a molecular probe may be operably bound.

Further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components and in various steps and arrangements of steps. The drawings are only for purposes of illustrating the preferred embodiments and are not to be construed as limiting the invention.

FIG. 7A is an image showing the photobleaching resistance, over time, of functionalized, fluorescent nanocrystals when exposed to a direct UV light source of a fluorescence microscope.

FIG. 7B is a graph showing the photobleaching resistance, over time, of functionalized, fluorescent nanocrystals when exposed to a direct UV light source of a fluorescence microscope.

FIG. 8A is a phase contrast image of a liver microscopic section treated with primary biotinylated antibodies against mouse IgG and stained with avidinylated, functionalized, fluorescent nanocrystals.

FIG. 8B is an image of the same section of FIG. BA, except using a fluorescence microscope.

DETAILED DESCRIPTION OF THE INVENTION

Definitions

Figure 1:
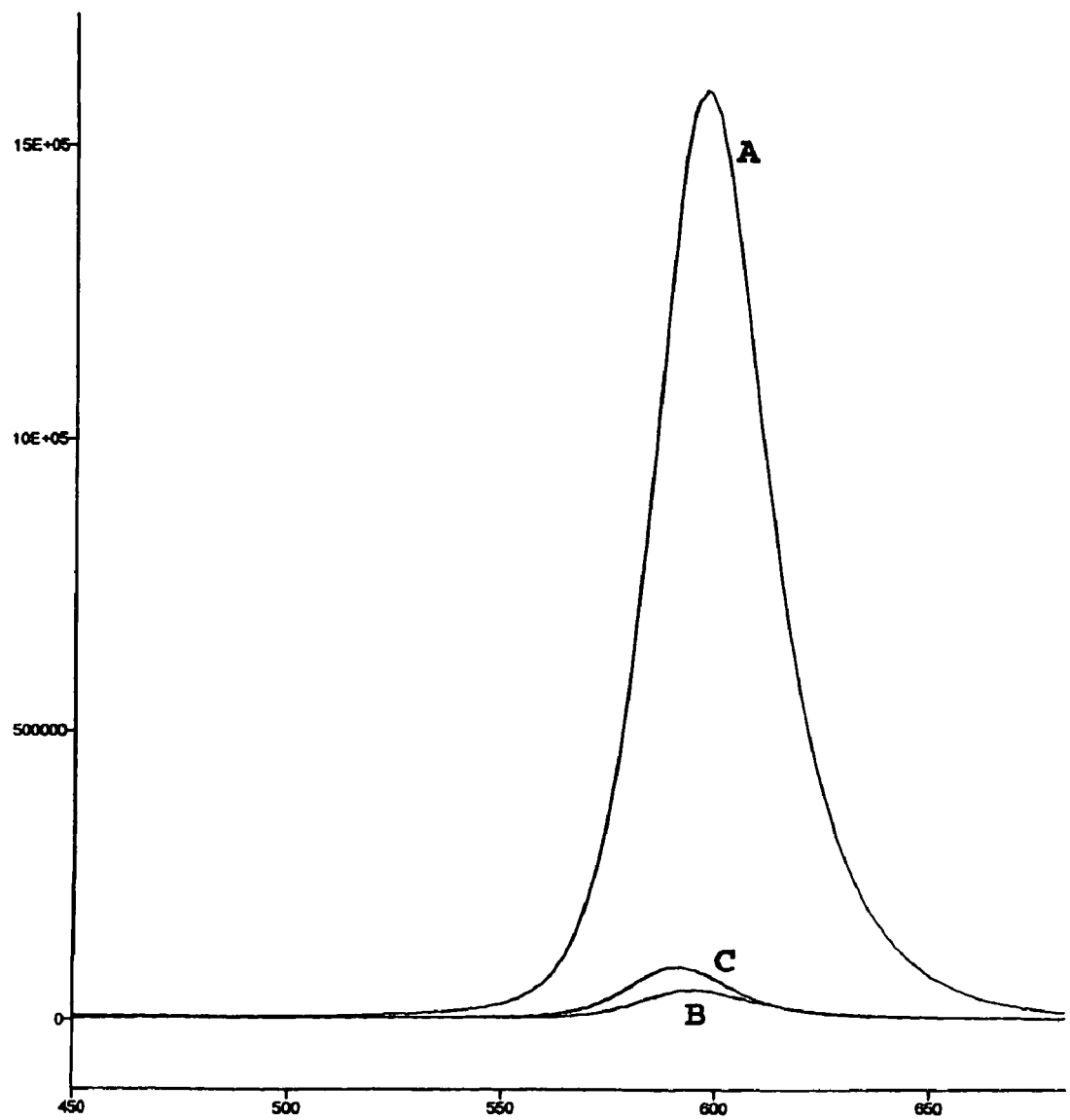
FIG. 1 is a graph showing an emission peak of functionalized, fluorescent nanocrystals (line A) as compared to peaks from other types of fluorescent nanocrystals (lines B & C).

Throughout the specification of the application, various terms are used such as "primary", "secondary", "first", "second", and the like. These terms are words of convenience in order to distinguish between different elements, and such terms are not intended to be limiting as to how the different elements may be utilized.

By the term "target molecule" is meant, for the purposes of the specification and claims to refer to a molecule of an organic or inorganic nature, the presence and/or quantity of which is being tested for; and which contains a molecular component (e.g., ligand or sequence or epitope or domain or portion or chemical group or reactive functionality or determinant, or the like) for which a molecular probe has binding specificity. The molecule may include, but is not limited to, a nucleic acid molecule, protein, glycoprotein, eukaryotic cell, prokaryotic cell, lipoprotein, peptide, carbohydrate, lipid, phospholipid, aminoglycans, chemical messenger, biological receptor, structural component, metabolic product, enzyme, antigen, drug, therapeutic, toxin, inorganic chemical, organic chemical, a substrate, and the like. The target molecule may be in vivo, in vitro, in situ, or ex vivo.

By the term "molecular probe" is meant, for purposes of the specification and claims, to mean a molecule which has binding specificity and avidity for a molecular component of, or associated with, a target molecule. In general, molecular probes are known to those skilled in the art to include, but are not limited to, lectins or fragments (or derivatives) thereof which retain binding function, monoclonal antibodies ("mAb", including chimeric or genetically modified monoclonal antibodies which may be preferable for administration to humans), peptides, aptamers, and nucleic acid molecules (including, but not limited to, single stranded RNA or single-stranded DNA, or single-stranded nucleic acid hybrids, oligonucleotide analogs, backbone. modified oligonucleotide analogs, morpholino-based polymers), and nucleobases. The term "nucleobase" is used herein to refer to a nucleic acid moiety including, but not limited to: nucleosides (including derivatives, or functional equivalents thereof, and synthetic or modified nucleosides, and particularly, a nucleoside comprising a reactive functionality (e.g., free amino group or carboxyl group)); nucleotides (including dNTPs, ddNTPs, derivatives or functional equivalents thereof, and particularly, a nucleotide comprising a reactive functionality (e.g., free amino group or carboxyl group); acyclonucleoside triphosphates (see, e.g., U.S. Pat. No. 5,558,991); 3'(2')-amino-modified nucleosides, 3'(2')-amino-modified nucleotides, 3'(2')-thiol-modified nucleosides, 3'(2')-thiol-modified nucleotides (see, e.g., U.S. Pat. No. 5,679,785; alkynylamino-nucleotides (see, e.g., as a chain terminator, U.S. Pat. No. 5,151,507); nucleoside thiotriphosphates (see, e.g., U.S. Pat. No. 5,187,085); and the like. The term "monoclonal antibody" is also used herein, for purposes of the specification and claims, to include immunoreactive fragments or derivatives derived from a mAb molecule, which fragments or derivatives retain all or a portion of the binding function of the whole mAb molecule. Such immunoreactive fragments or derivatives are known to those skilled in the art to include F(ab')2, Fab', Fab, Fv, scFV, Fd' and Fd fragments. Methods for producing the various fragments or derivatives from mAbs are well known in the art (see, e.g., Pluckthum., 1992, Immunol. Rev. 130:152–188; for example, via pepsin digestion, papain digestion, reduction of disulfide bridges, and methods described in U.S. Pat. No. 4,642,334). Single chain antibodies can be produced as described in U.S. Pat. No. 4,946,778. The construction of chimeric antibodies is now a straightforward procedure (Adair, 1992, *Immunological Reviews* 130: 5–40) in which the chimeric antibody is made by joining the murine variable region to a human constant region. Additionally, "humanized" antibodies may be made by joining the hypervariable regions of the murine monoclonal antibody to a constant region and portions of variable region (light chain and heavy chain) sequences of human immunoglobulins using one of several techniques known in the art (Adair, 1992, supra; Singer et al., 1993, *J. Immunol.* 150:2844–2857). Methods for making a chimeric non-human/human mAb in general are described in detail in U.S. Pat. No. 5,736,137. Aptamers can be made using methods described in U.S. Pat. No. 5,789,157. Lectins and fragments thereof are commercially available. Oligonucleotide analogs, backbone modified oligonucleotide analogs, and morpholino-based polymers can be made using methods described in U.S. Pat. Nos. 5,969,135, and 5,596,086, U.S. Pat. Nos. 5,602,240, and 5,034,506, respectively. "Molecular probe" may also be used herein to refer to a plurality of molecules of molecular probe which may be operably bound to a functionalized, fluorescent nanocrystal.

By the terms "operably bind" and "operably bound" are meant, for purposes of the specification and claims to refer to fusion or bond or an association, of sufficient stability for the purposes of use in detection systems as described herein and standard conditions associated therewith as known in the art, formed between a combination of different molecules including, but not limited to, between a coating compound and fluorescent nanocrystal, between a coating and molecular probe, between different molecular probes, and between molecular probe and target molecule. As known to those skilled in the art, and as will be more apparent by the following embodiments, there are several methods and compositions in which two or more molecules may be operably bound utilizing reactive functionalities. Reactive functionalities include, but are not limited to, bifunctional reagents (e.g., homobifunctional or heterobifunctional), biotin, avidin, free chemical groups (e.g., thiol, or carboxyl, hydroxyl, amino, amine, sulfo, and the like), and reactive chemical groups (reactive with free chemical groups). As known to those skilled in the art, the bond may comprise, but is not limited to, one or more of: covalent, ionic, hydrogen, van der Waals, and the like.

By the term "imidazole-containing compound" is meant, for purposes of the specification and claims to refer to a molecule that has at least one imidazole group (e.g., imidazole ring) available for binding a metal such as zinc or other metal cation, or substrate containing such cation. In that respect, preferably at least one imidazole moiety is in a terminal position with respect to the structure of the molecule. Generally, imidazole ring nitrogens frequently serve as coordinating ligand to operably bind a metal ion such as zinc or cadmium. In one embodiment, the imidazole-containing compound comprises an amino acid, or two or more amino acids joined together (e.g., known in the art as "peptidyl" or "oligopeptide"), which may include, but is not limited to, histidine, carnosine, anserine, baleine, homocarnosine, 1-methylhistidine, 3-methylhistidine, imidazolysine, imidazole-containing ornithine (e.g., 5-methylimidazolone), imidazole-containing alanine (e.g., (beta)-(2-imidazolyl)-L(alpha)alanine), carcinine, histamine, and the like. Imidazole-containing amino acids may be synthesized using methods known in the art (see, e.g., Stankova et al., 1999, *J. Peptide Sci.* 5:392–398, the disclosure of which is herein incorporated by reference).

By the term "amino acid" is meant, as known in the art and for purposes of the specification and claims, to refer to a compound containing at least one amino group and at least one carboxyl group. As known in the art, an amino group may occur at the position adjacent to a carboxyl group, or may occur at any location along the amino acid molecule. In addition to at least one imidazole moiety, the amino acid may further comprise one or more additional reactive functionalities (e.g., amino, thiol, carboxyl, carboxamide, etc.). The amino acid may be a naturally occurring amino acid, a synthetic amino acid, a modified amino acid, an amino acid derivative, an amino acid precursor, in D (dextro) form, or in L (levo) form. Examples of derivatives may include, but is not limited to, an N-methylated derivative, amide, or ester, as known in the art, and where consistent with the functions of the amino acid as a coating as described herein (e.g., imparts water-solubility, buffers sufficiently in a pH range between about pH 6 and about pH 10, functions as a coat which can increase fluorescence intensity, and has one or more reactive functionalities that may be used to operably bind molecular probe). An amino acid of the aforementioned amino acids may be used in a preferred embodiment, and a preferred amino acid may be used separately in the composition of the present invention to the exclusion of amino acids other than the preferred amino acid. Histidine is a particularly preferred imidazole-containing compound for coating the functionalized, fluorescent nanocrystals according to the present invention.

By the term "phosphine cross-linking compound" is meant, for purposes of the specification and claims to refer to a molecule that has at least one phosphine group (e.g., in the form of phosphine, phosphine oxide, or phosphonium) available for binding or chelating a metal such as Zn, Cd, or the like and/or a non metal such as Se, S or other non metals, or substrate containing such atoms, and has at least one reactive functionality (e.g., hydroxyl, amino, thiol, carboxyl, carboxamide, etc.) with ability to react with neighboring molecules. Phosphine cross-linking compounds are known to those skilled in the art to include, but are not limited to, diphosphines, triphosphines, alkyl phosphines (including alkyl phosphine containing compounds), cycloalkyl phosphine, aryl phosphine, bidentate phosphine, silicone derivatives of phosphine, siloxane or polysilane derivatives of phosphine, olefinic phosphines, and the like. A preferred phosphine cross-linking compound for one embodiment of the present invention is alkyl phosphine. In that respect, preferably at least one phosphine moiety is in a terminal position with respect to the structure of the molecule. Generally, phosphine moieties frequently serve as coordinating ligand to operably bind a metal such as Zn, Cd, and/or a non metal ion such as Se or S. In a preferred embodiment, the phosphine cross-linking compound comprises a phosphine group, or two or more phosphine groups joined together (e.g., in a polymeric form), which may include, but is not limited to, hydroxymethylphosphine compounds, and the like. Phosphine cross-linking compounds may be synthesized using methods known in the art (see, e.g., Tsiavaliaris et al., 2001, Synlett. 3: 391–393, Hoffman et al, 2001, Bioconjug Chem 12: 354–363, U.S. Pat. No. 5,948,386). As known in the art, an alkyl phosphine-containing compound may further comprise one or more additional reactive functionalities (e.g., hydroxyl, amino, thiol, carboxyl, carboxamide, etc.). Examples of derivatives may include, but is not limited to, a hydroxy methyl phosphine derivative, amide, or ester, as known in the art, and where consistent with the functions of the alkyl phosphine as a coating as described herein (e.g., imparts water-solubility, buffers sufficiently in a pH range between about pH 6 and about pH 10, functions as a coat and cross-linker which can increase stability and fluorescence intensity, and has one or more reactive functionalities that may be used to operably bind molecular probe). An alkyl phosphine of the aforementioned derivatives may be used in a preferred embodiment. A preferred phosphine cross-linking compound may be used to the exclusion of phosphine cross-linking compounds other than the preferred phosphine cross-linking compound. Tris(hydroxy methyl)phosphine and beta-[Tris(hydroxymethyl)phosphino]propionic acid are particularly preferred alkyl phosphine-containing compound for coating, stabilizing and functionalizing fluorescent nanocrystals according to the present invention. In a preferred embodiment, cross-linking compounds comprising alkyl phosphine-containing compounds have additional ability to operably bind to metal ions such as zinc and cadmium.

By the term "fluorescent nanocrystals" is meant, for purposes of the specification and claims to refer to nanocrystals comprising semiconductor nanocrystals or doped metal oxide nanocrystals, to which may be operably bound imidazole and phosphonium containing compounds. "Semiconductor nanocrystals" is meant, for purposes of the specification and claims to refer to quantum dots (also known as crystallite semiconductors) comprised of a core comprised of at least one of a Group II–VI semiconductor material (of which ZnS, and CdSe are illustrative examples), or a Group III–V semiconductor material (of which GaAs is an illustrative example), or a Group IV semiconductor material, or a combination thereof. The semiconductor nanocrystal may further comprise a semiconductor material comprising a shell, as described herein in more detail. As known to those skilled in the art, the size of the core of the semiconductor nanocrystal correlates with the spectral range of emission. Table 1 is an illustrative example for CdSe.

TABLE 1

| Color | Size Range (nm) | Peak Emission Range |
|---|---|---|
| Blue | 2.1 to 2.9 | 436 to 500 |
| Green | 2.9 to 4.7 | 500 to 575 |
| Yellow | 4.7 to 5.0 | 575 to 592 |
| Orange | 5.0 to 6.1 | 592 to 620 |
| Red | 6.1 to 10.2 | 620 to 650 | in a preferred embodiment, the semiconductor nanocrystals are produced using a continuous flow process and system (see, U.S. Pat. No. 6,179,912), and have a particle size that varies by less than +/−4% in the average particle size. In a preferred embodiment, the semiconductor nanocrystals comprise a monodiesperse population having an average particle size (as measure by diameter) in the range of approximately 1 nanometer (nm) to approximately 20 nm.

By the term "doped metal oxide nanocrystals" is meant, for purposes of the specification and claims to refer to nanocrystals comprised of: a metal oxide, and a dopant comprised of one or more rare earth elements. For example, metal oxides include, but are not limited to, yttrium oxide ($Y_2O_3$), zirconium oxide ($ZrO_2$), zinc oxide (ZnO), copper oxide (CuO or $Cu_2O$), gadolinium oxide ($Gd_2O_3$), praseodymium oxide ($Pr2O_3$), lanthanum oxide ($La_2O_3$), and alloys thereof. The rare earth elements comprises an element selected from the Lanthanide series and include, but is not limited to, europium (Eu), cerium (Ce), neodymium (Nd), samarium (Sm), terbium (Th), gadolinium (Gd), holmium (Ho), thulium (Tm), an oxide thereof, and a combination thereof. As known to those skilled in the art, depending on the dopant, an energized doped metal oxide nanocrystal is capable of emitting light of a particular color. Thus, the nature of the rare earth or rare earths are selected in consequence to the color sought to be imparted (emitted) by a doped metal oxide nanocrystal used to label a microsphere according to the present invention. A given rare earth element or rare earth elements combination has a given color, thereby permitting the provision of doped metal oxide nanocrystals, each of which may emit (with a narrow emission peak) a color over an entire range of colors by adjusting the nature of the dopant, the concentration of the dopant, or a combination thereof. For example, the emission color and brightness (e.g., intensity) of a doped metal oxide nanocrystal comprising $Y_2O_3$:Eu may depend on the concentration of Eu; e.g., emission color may shift from yellow to red with increasing Eu concentration. For purposes of illustration only, representative colors which may be provided are listed in Table 2.

TABLE 2

| Fluorescent Color | Dopant |
|---|---|
| Blue | Thulium |
| Blue | Cerium |
| Yellow-green | Terbium |
| Green | Holmium |
| Green | Erbium |
| Red | Europium |
| Reddish orange | Samarium |
| Orange | Neodymium |
| Yellow | Dysprosium |
| White | Praseodymium |
| Orange-yellow | Europium + terbium |
| Orange-red | Europium + samarium |

Methods for making doped metal oxide nanocrystals are known to include, but are not limited to, a sol-gel process (see, e.g., U.S. Pat. No. 5,637,258), and an organometallic reaction. As will be apparent to one skilled in the art, the dopant (e.g., one or more rare earth elements) are incorporated into the doped metal oxide nanocrystal in a sufficient amount to permit the doped metal oxide nanocrystal to be put to practical use in fluorescence detection as described herein in more detail. An insufficient amount comprises either too little dopant which would fail to emit sufficient detectable fluorescence, or too much dopant which would cause reduced fluorescence due to concentration quenching. In a preferred embodiment, the amount of dopant in a doped metal oxide nanocrystal is a molar amount in the doped metal oxide nanocrystal selected in the range of from about 0.1% to about 25%. Doped metal oxide nanocrystals can be excited with a single excitation light source resulting in a detectable fluorescence emission of high quantum yield (e.g., a single nanocrystal having at a fluorescence intensity that may be a log or more greater than that a molecule of a conventional fluorescent dye) and with a discrete fluorescence peak. Typically, they have a substantially uniform size of less than 200 Angstroms, and preferably have a substantially uniform size in the range of sizes of from about 1 m to about 5 nm, or even less than 1 nm. In a preferred embodiment, the doped metal oxide nanocrystals are comprised of metal oxides doped with one or more rare earth elements, wherein the dopant comprising the rare earth element is capable of being excited (e.g., with ultraviolet light) to produce a narrow spectrum of fluorescence emission. In another preferred embodiment, the doped metal oxide has both fluorescent properties (when excited with an excitation light source) and magnetic properties; thus, a polymeric microsphere (which is substantially nonmagnetic) embedded or labeled with a plurality of fluorescent nanocrystals (comprising doped metal oxide nanocrystals which are magnetic material) may form fluorescent microspheres which are magnetic.

By the term "functionalized, fluorescent nanocrystals" is meant, for purposes of the specification and claims to refer to fluorescent nanocrystals which are coated with a coating comprising imidazole-containing compound alone, or an imidazole-containing compound and phosphine cross-linking compound. Functionalized, fluorescent nanocrystals according to the present invention demonstrate desired properties which include (but are not limited to): water-solubility; the ability to be operably bound, via one or more reactive functionalities, to molecular probe, (c) an increase in fluorescence intensity when excited by a suitable excitation light source (see, e.g., Example 1, 2, 3, and FIGS. 5–8 herein); and may further demonstrate chemical stability in a pH range of from about pH 6.0 to about pH 10.5. Preferred functionalized, fluorescent nanocrystals may be produced, and used in the method and system as according to present invention, to the exclusion of functionalized, fluorescent nanocrystals other than the preferred functionalized, fluorescent nanocrystals. In a preferred embodiment to form the functionalized, fluorescent nanocrystals according to the present invention, a core nanocrystal may be coated by the coprecipitation of a compound comprising a metal cation (e.g., for forming a semiconductor material, preferably with a high band gap energy, as known in the art; "shell") operably bound to an imidazole-containing compound alone, or an imidazole-containing compound and a phosphine cross-linking compound, wherein the coat is uniformly deposited over the outer surface of the nanocrystal core. This is both functionally and fundamentally different than using zinc-histidine as nucleation centers for growing core nanocrystals (see, Kho et al., 2000, Biochem. Biophys. Res. Commun. 272:29–35). As an example of this preferred embodiment, a Group II–VI semiconductor core may be coated with a Group II–VI semiconductor shell (e.g., a ZnS or CdSe core may be coated with a shell comprised of YZ wherein Y is Cd or Zn, and Z is S, or Se) and an imidazole-containing compound or an imidazole-containing compound cross-linked with an alkyl phosphine-containing compound. Preferably, the coating comprised of the semiconductor material (shell) and imidazole-containing compound, as well as alkyl phosphine-containing compound, passivates the outer surface of the core nanocrystal onto which it is deposited.

In another, preferred embodiment, a core/shell nanocrystal (e.g., CdX core/YZ shell) produced using methods standard in the art is coated with a metal cation (preferably capable of forming a semiconductor material, preferably, with a high band gap energy) operably bound to an imidazole-containing compound alone or an imidazole-containing compound cross-linked with an alkyl phosphine-containing compound, wherein the coat is uniformly deposited over the outer surface of the core/shell nanocrystal.

In yet another embodiment, a fluorescent nanocrystal may be coated with imidazole-containing compound alone or an imidazole-containing compound cross-linked with phosphine cross-linking compound, to produce the functionalized, fluorescent nanocrystals according to the present invention.

In another embodiment, onto the outer surface of a core/shell nanocrystal is deposited a coating comprising imidazole-containing compound alone or an imidazole-containing compound and alkyl phosphine-containing compound.

In another preferred embodiment, the functionalized, fluorescent nanocrystal according to the present invention further comprises chemical or physical cross-linking of the coating comprising imidazole containing compound, and alternatively, imidazole-containing compound and alkyl phosphine-containing compound, to promote further stabilization of the coat of the functionalized, fluorescent nanocrystal. Chemical cross-linking can be achieved by using methods and reagents known in the art which may include, but is not limited to, formaldehyde, glutaraldehyde, acrolein, 1,6-hexane-bis-vinylsulfone, and the like. Physical cross-linking and/or curing can also be achieved by using methods known in the art which may include, but is not limited to, ultraviolet irradiation, microwave treatment, heat treatment, and the like.

The present invention provides compositions comprising functionalized, fluorescent nanocrystals which can be used in a variety of types of fluorescence-based detection systems which include, but are not limited to, use to build three dimensional dendrimers which function to generate and significantly amplify a detectable signal (thereby considerably improving the sensitivity of a non-isotopic detection system; see, e.g., U.S. Pat. No. 6,261,779, the disclosure of which is herein incorporated by reference); use to label nucleobases in providing fluorescence-labeled nucleobases for nucleic acid strand synthesis or nucleic acid sequence determination (see, e.g., U.S. Pat. No. 6,221,602, the disclosure of which is herein incorporated by reference); use for producing fluorescent microspheres (e.g., beads) by either embedding microspheres with and/or to operably bind microspheres to, functionalized, fluorescent nanocrystals; use in fluorescent ink compositions suitable for printing on substrates; and for providing a substrate with an identifiable code pattern by applying to the substrate the functionalized, fluorescent nanocrystals in a manner to establish an identifiable code pattern (e.g., for purposes of identification, verification, security, or ornamental).

As will be apparent to one skilled in the art, the functionalized, fluorescent nanocrystals according to the present invention may be used in a detection system that may include, but is not limited to, one or more of: an affinity assay (e.g., immunoassay such as an ELISA), fluorescent staining (e.g., immunofluorescent staining on a glass slide, fluorescent in situ hybridization, and the like), flow cytometry, cell imaging-based detection assays (e.g., cell-based ELISA or "cELISA", image cytometry, cells grown in standard high. density microarrays), microarray-based detection assays (e.g., oligonucleotide scanning arrays, combinational DNA arrays, microchips containing arrays of nucleic acid molecules or protein molecules, multi-channel microchip electrophoresis, and the like), microfluidics-based detection assays (e.g., "lab-on-a-chip" systems as known in the art), fluorescence-based biosensors (see, e.g., Trends in Biotech. 16:135–140, 1998; may include implantable sensors for determination of a target molecule in vivo), nucleic acid sequencing, nucleic acid hybridization, nucleic acid synthesis or amplification, identification verification (e.g., identification card or bank card), fluorescent bead-based detection assays, molecular sorting (e.g., cell sorting by flow cytometry), and the like.

Such functionalized, fluorescent nanocrystals can be used to detect the presence or absence of a target molecule. Also provided is a method for detecting the presence or absence of target molecule in a sample. The process for detecting such target molecule includes contacting the composition comprising functionalized, fluorescent nanocrystals operably bound to molecular probe with the sample, exposing the sample to an excitation light source, and detecting fluorescence emitted by the functionalized, fluorescent nanocrystals. The amount of fluorescence detected can then be correlated with the amount of target molecule present in the sample.

EXAMPLE 1

This example illustrates embodiments of a process of making the functionalized, fluorescent nanocrystals according to the present invention. For this and subsequent examples, semiconductor nanocrystals comprising core nanocrystals were produced using a continuous flow process as described in U.S. Pat. No. 6,179,912. The following parameters were used to produce nanocrystals of cadmium selenide (CdSe): 10 g TOPO; 18.9 ul of Me$_2$Cd (dimethyl cadmium; e.g., $2.63 \times 10^{-4}$ moles of Cd); 1989 μl of TOPSe (1M solution of Se in TOP; e.g., $1.989 \times 10^{-4}$ moles of Se); 4.5 ml of TOP; nucleation temperature ($T_n$) of 300° C.; growth temperature ($T_g$) of 280° C.; and flow rate of 0.1 ml/min. The resulting CdSe nanocrystals displayed fluorescence at a wavelength of 578 nm, with an excitation wavelength of 410 nm, and a narrow half height band width of about 29 nm.

In one embodiment, the process of making functionalized, fluorescent nanocrystals includes contacting a solution comprising imidazole-containing compound with a solution comprising a metal cation in producing a mixture including complexes comprised of imidazole-containing compound operably bound to metal cation; and contacting the mixture with fluorescent nanocrystals in forming a coating over the fluorescent nanocrystals in producing functionalized, fluorescent nanocrystals.

In another embodiment, the process of making functionalized, fluorescent nanocrystals includes contacting a solution comprising imidazole-containing compound with a fluorescent nanocrystal comprising a metal cation, wherein the imidazole-containing compound operably binds to the metal cation in producing a coat over the fluorescent nanocrystals in forming functionalized, fluorescent nanocrystals.

As previously described herein in more detail, the fluorescent nanocrystals which are coated by the process may comprise core semiconductor nanocrystals, core/shell semiconductor nanocrystals, doped metal oxide nanocrystals, or a combination thereof. With respect to metal cations, imidazole-containing compounds have been reported to operably bind metal ions which may include, but are not limited to one or more of, $Zn^{2+}$ $Cu^{2+}$, $Fe^{2+}$, $Ni^{2+}$, $Cd^{2+}$, $Co^{2+}$, and the like.

For example, core nanocrystals were coated to produce the functionalized, fluorescent nanocrystals according to the present invention. In one embodiment, the core nanocrystals were coated by a mixture which comprised complexes comprised of metal cation operably bound to imidazole-containing compound. Preferably, the metal cation comprises Zn operably bound to a sulfur containing compound (e.g., sulfate, sulfide, and the like). More preferably, the metal cation comprises semiconductor material ("shell"; preferably, with a high band gap energy, as known in the art). As a general guideline, the coating process may comprise inclusion of components comprising, per milligram of fluorescent nanocrystals: metal cation (e.g., $ZnSO_4$) in an amount ranging from about 0 mmole to about 0.5 mmole; imidazole-containing compound in an amount ranging from about 0.25 mmole to about 2.5 mmole; and $Na_2S$ in an amount ranging from 0 to 1 mmole. As apparent to one skilled in the art, the amount of each individual component may vary depending on the particular imidazole-containing compound used, the nature (e.g., chemical composition) of fluorescent nanocrystal to be coated, the nature of the metal cation to which is operably bound the imidazole-containing compound, the ratio of other components in the coating process, and the pH of the buffer system used in the coating process.

For example, prepared was a 0.25 M histidine (imidazole-containing compound) solution in a 1 M Tris buffer (pH 10.6). Other suitable buffers known in the art which provide buffering in a range of from about pH 8.0 to about pH 11, may be used in place of the Tris buffer (e.g., a sodium carbonate buffer, TAPS buffer (N-tris(hydroxymethyl)methyl-3aminopropanesulfonic acid), CAPSO buffer (3-(cyclohexylamino)2-hydroxy-1 propanesulfonic acid), and the like). To 10 ml of the histidine solution was added 1.2 ml of a 1 M zinc sulfate solution (in 1 M HCl) with mixing until the mixture turned clear. To the mixture was added 2 to 3 mg of CdSe nanocrystals (core nanocrystals) suspended in a minimal volume (e.g., from about 60 μl to about 80 μl) of organic solvent (e.g., chloroform or pyridine). After mixing, also added was 1.2 ml of 1M $Na_2S$. The resultant solution was mixed gently for several hours (e.g., for a period of about 4 to about 16 hours) at room temperature. The pH of the resulting solution; comprising the functionalized, fluorescent nanocrystals, was about 9.6. The functionalized, fluorescent nanocrystals were then purified by a process selected from the group consisting of: size exclusion chromatography, dialysis, precipitation with alcohol (e.g., ethanol), centrifugation, and a combination thereof. For example, the solution comprising functionalized, fluorescent nanocrystals was applied onto a gel filtration column (e.g., desalt dextran) equilibrated with the Tris buffer. Functionalized fluorescent nanocrystals harvested from the chromatographic process were then concentrated using a low speed, centrifugation filter system (cut off of 10,000 daltons). This process for making the functionalized, fluorescent nanocrystals was repeated, whereby the relative amounts of each component were varied. From these formulation studies, a preferred ratio of components that showed optimal properties of fluorescence and stability (in an aqueous environment) comprises: 1 mg of core nanocrystals (e.g., CdSe); 1.25 mmole histidine; 0.25 mmole $ZnSO_4$, and 0.5 mmole $Na_2S$. The resultant functionalized, fluorescent nanocrystals were characterized by: stability in aqueous solutions of the general pH range of about 7 to about 10, with optimal stability in the range of from about pH 8 to about pH 10; available reactive functionalities on the surface of the functionalized, fluorescent nanocrystals (in this case, both amino groups and carboxyl groups) to which molecular probe may be operably bound; and an enhancement of fluorescence intensity of between about 10 fold to about 100 fold when compared to fluorescence intensity of CdSe/ZnS nanocrystals capped with mercaptoacetic acid. The comparison of fluorescence intensity was made with an equivalent amount of fluorescent nanocrystals made using core nanocrystals from the same run in the continuous flow process as the core nanocrystals coated with the process according to the present invention; excitation with the same excitation light source (e.g., 410 nm); and detection using the same detection system. The detection system used was a standard spectrofluorometer, wherein the instrument's software calculated the area under the acquired emission peak as a measurement of fluorescence intensity, as standard in the art. With respect to measurement of stability, less than optimal stability was characterized by one or more of a tendency for the functionalized, fluorescent nanocrystals to aggregate over time when present in an aqueous solution, or a loss of fluorescence intensity (e.g., loss of the observed enhancement or loss of any detectable emission at all) associated with functionalized, fluorescent nanocrystals.

The process of making functionalized, fluorescent nanocrystals, and the functionalized, fluorescent nanocrystals themselves, may further comprise cross-linking of the coating. Cross-linking of the coating (e.g., the reactive functionalities thereof) may provide, as compared to functionalized, fluorescent nanocrystals without cross-linking, one or more of: increased overall stability such as with respect to water solubility; enhanced ability to operably bind molecular probe; and better tolerance toward various physicochemical processes (e.g., centrifugation, dialysis, temperature changes, and the like). As apparent to one skilled in the art, there are numerous cross-linking reagents known in the art, and the choice of a cross-linking reagent will depend on the reactive functionalities present on the coating (and hence, the type of imidazole-containing compound used for coating). Preferred reactive functionalities to cross-link include amino groups, carboxyl groups, and a combination thereof. As an illustrative example, functionalized, fluorescent nanocrystals were treated with one or more amino-reactive crosslinking agents (e.g., glutaraldehyde, formaldehyde, acrolein, 1,6-hexane-bisvinylsulfone, and the like). For example, 500 μl of the functionalized, fluorescent nanocrystals (10 mg solid materials) was precipitated by 70% ethanol, centrifuged, and the resulting pellet was redissolved in 500 μl of 0.5 M Hepes buffer (pH 8.0). This solution was immediately mixed with equal volume of glutaraldehyde solution (0.02% in 0.5M Hepes buffer, pH 8.0). Following a short incubation (e.g., from about 2 to about 5 minutes) at room temperature, the reaction was quenched by the addition of 20 mM Tris or addition of hydroxylamine. As an alternative, the reaction was quenched with penicillamine (e.g., about 100 mM) because it showed better quenching and clarifying effects than use of a Tri s-based reagent. To remove the excess reagents (e.g., crosslinkers and quenchers), ethanol precipitation was performed, and the final pellet was redissolved in 500 µl of 0.5 M Hepes buffer (pH 7.5–8.0). The functionalized, fluorescent nanocrystals, further comprising the cross-linking of the outer coat, have also been used successfully in operably binding molecular probe, and in detection assays for target molecule.

EXAMPLE 2

In another embodiment, fluorescent nanocrystals comprising core/shell nanocrystals are coated by a coating comprising metal cation operably bound to imidazole-containing compound. Preferably, the metal cation comprises Zn operably bound to a sulfur-containing compound (e.g., sulfate, sulfide, and the like). As a general guideline, the coating process may comprise inclusion of components comprising, per 2 milligrams of core/shell nanocrystals: metal cation (preferably comprising a semiconductor material, e.g., YZ; and more preferably, $ZnSO_4$), in an amount ranging from about 0 mmole to about 0.5 mmole; imidazole-containing compound in an amount ranging from about 0.25 mmole to about 2.5 mmole; and $Na_2S$ in an amount ranging from 0 to 1 mmole. As apparent to one skilled in the art, the amount of each individual component may vary depending on the particular imidazole-containing compound used, the nature (e.g., chemical composition) of fluorescent nanocrystal to be coated, the nature of the metal cation to which is operably bound the imidazole-containing compound, the ratio of other components in the coating process, and the pH of the buffer system used in the coating process. For example, when using zinc as a metal cation and histidine as imidazole containing compound, and since each zinc ion operably binds two or more histidine molecules, it is desirable that in the coating process the number of histidine molecules be at least 2-fold more the number of zinc ions. In another example, and with respect to the range of the amount of the imidazole containing compound used in the coating process, a higher amount of the imidazole-containing compound may produce a greater degree of solubility or stability in aqueous solutions, but may also lead to a decrease in the unexpected enhancement of fluorescence intensity.

Figure 2:
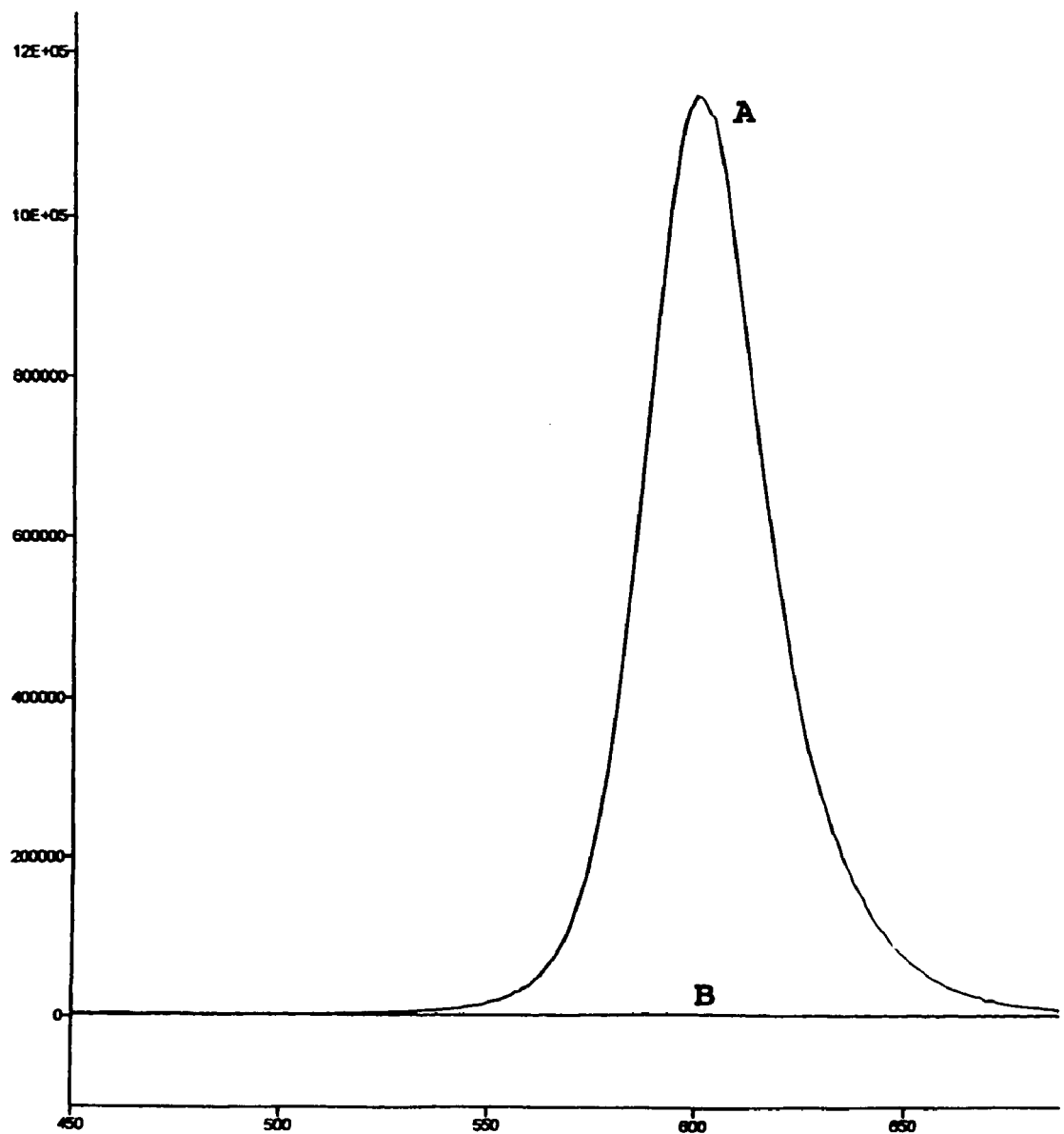
FIG. 2 is a graph showing an emission peak of functionalized, fluorescent nanocrystals (line A) as compared to an emission peak from another type of fluorescent nanocrystals (lines B).

In illustrating this embodiment, prepared was a 0.25 M histidine (imidazole-containing compound) solution in a 1 M Tris buffer (pH 10.6). As previously described herein, other suitable buffers are known in the art. To 10 ml of the histidine solution was added 1.2 ml of a 1 M zinc sulfate solution (in HCl) with mixing until the mixture turned clear. To the mixture was added 3 to 4 mg of CdSe (core)/ZnS (shell)-fluorescent nanocrystals suspended in a minimal volume (e.g., from about 60 µl to about 80 µl) of organic solvent (e.g., chloroform or pyridine). After mixing, also added was 1.2 ml of 1M $Na_2S$. The resultant solution was mixed gently for several hours at room temperature. The pH of the resulting solution, comprising the functionalized, fluorescent nanocrystals, was about 9.6. The functionalized, fluorescent nanocrystals were then purified as previously described herein. This process for making the functionalized, fluorescent nanocrystals was repeated, whereby the relative amounts of each component were varied. From these formulation studies, a preferred ratio of components that showed optimal properties of fluorescence and stability (in an aqueous environment) comprises: 2 mg of core/shell fluorescent nanocrystals (e.g., CdSe/ZnS); 1.25 mmole histidine; 0.25 mmole $ZnSO_4$, and 0.5 mmole $Na_2S$. The resultant functionalized, fluorescent nanocrystals were characterized by: stability in aqueous solutions of the general pH range of about 7 to about 10, with maximum stability in the range of from about pH 8 to about pH 10; a submicron particle size of about 20.6 nm (with a standard deviation of about 3.8 nm); availability of reactive functionalities on the surface of the functionalized, fluorescent nanocrystals (in this case, both amino groups and carboxyl groups) to which molecular probe may be operably bound; and an unexpected increase in fluorescence intensity, comprising at least about 30 fold to as much as about 300 fold or more (see, e.g., FIGS. 1 & 2, line A), when compared to fluorescent intensity of either CdSe/ZnS fluorescent nanocrystals capped with a mercapto-based compound (e.g., mercapto-acetic acid) as known in the art (FIGS. 1 & 2, line B) or CdSe/ZnS fluorescent nanocrystals (FIG. 1, line C).

The comparison of fluorescence intensity was made with an equivalent amount of CdSe/ZnS fluorescent nanocrystals (which were either uncoated or capped with mercapto-based compound) as that used as starting material to be coated with the process according to the present invention; excitation with the same excitation light source (e.g., 410 nm); and detection using the same detection system. Thus, in accordance with the present invention, the process of coating results in, and resultant functionalized, fluorescent nanocrystals comprise, a coating that provides at least about a 30 fold increase in fluorescence intensity than comparable fluorescent nanocrystals known in the art (e.g., CdX/YZ fluorescent nanocrystals or CdX/YZ fluorescent nanocrystals capped with mercapto-based compound)(see, e.g., FIG. 1). Such an increase is an unexpected result with respect to the degree of enhancement of fluorescence intensity. In a more preferred embodiment of the present invention, the process of coating results in, and resultant functionalized, fluorescent nanocrystals comprise, a coating that provides at least about a 300 fold increase in fluorescence intensity than comparable fluorescent nanocrystals known in the art (e.g., CdX/YZ fluorescent nanocrystals or CdX/YZ fluorescent nanocrystals capped with mercapto-based compound)(see, e.g., FIG. 2). Such an increase is an unexpected result with respect to the degree of enhancement of fluorescence intensity. In another embodiment, these functionalized, fluorescent nanocrystals were further treated by cross-linking using the methods as previously described in Example 1 herein.

EXAMPLE 3

In this example, provided is another embodiment of process of making functionalized, fluorescent nanocrystals by coating fluorescent nanocrystals with a coating comprising metal cation operably bound to imidazole-containing compound. In this example, the metal cation comprises Zn operably bound to a sulfur-containing compound (e.g., sulfate, sulfide, and the like), and the imidazole-containing compound comprises carnosine. Carosine is a dipeptide comprising (alpha)-alanyl1-histidine). As a general guideline, the coating process may comprise inclusion of components comprising, per 2 milligrams of core/shell nanocrystals: metal cation (preferably, $ZnSO_4$), in an amount ranging from about 0 mmole to about 0.5 mmole; imidazole-containing compound in an amount ranging from about 0.25 mmole to about 0.5 mmole; and $Na_2S$ in an amount ranging from 0 to 1 mmole. As apparent to one skilled in the art, the, amount of each individual component may vary depending on the particular imidazole-containing compound used, the nature (e.g., chemical composition) of fluorescent nanocrystal to be coated, the nature of the metal cation to which is operably bound the imidazole-containing compound, the ratio of other components in the coating process, and the pH of the buffer system used in the coating process.

For example, prepared was a 0.5 M carnosine (imidazole-containing compound) solution in a 1 M Tris buffer (pH 10.6). As previously described herein, other suitable buffers are known in the art. To 10 ml of the carnosine solution was added 1.2 ml of a 1 M zinc sulfate solution (in HCl) with mixing until the mixture turned clear. To the mixture was added 3 to 4 mg of CdSe (core)/ZnS (shell) fluorescent nanocrystals suspended in a minimal volume (e.g., from about 60 μl to about 80 μl) of organic solvent (e.g., chloroform or pyridine). After mixing, also added was 1.2 ml of 1 M $Na_2S$. The resultant solution was mixed gently for several hours at room temperature. The pH of the resulting solution, comprising the functionalized, fluorescent nanocrystals, was about 9.6. The functionalized, fluorescent nanocrystals were then purified as previously described herein. This process for making the functionalized, fluorescent nanocrystals was repeated, whereby the relative amounts of each component were varied. From these formulation studies, a preferred ratio of components that showed optimal properties of fluorescence and stability (in an aqueous environment) comprises: 2 mg of core/shell fluorescent nanocrystals (e.g., CdSe/ZnS); 2.5 mmole carnosine; 0.25 mmole $ZnSO_4$, and 0.5 mmole $Na_2S$.

Figure 3:
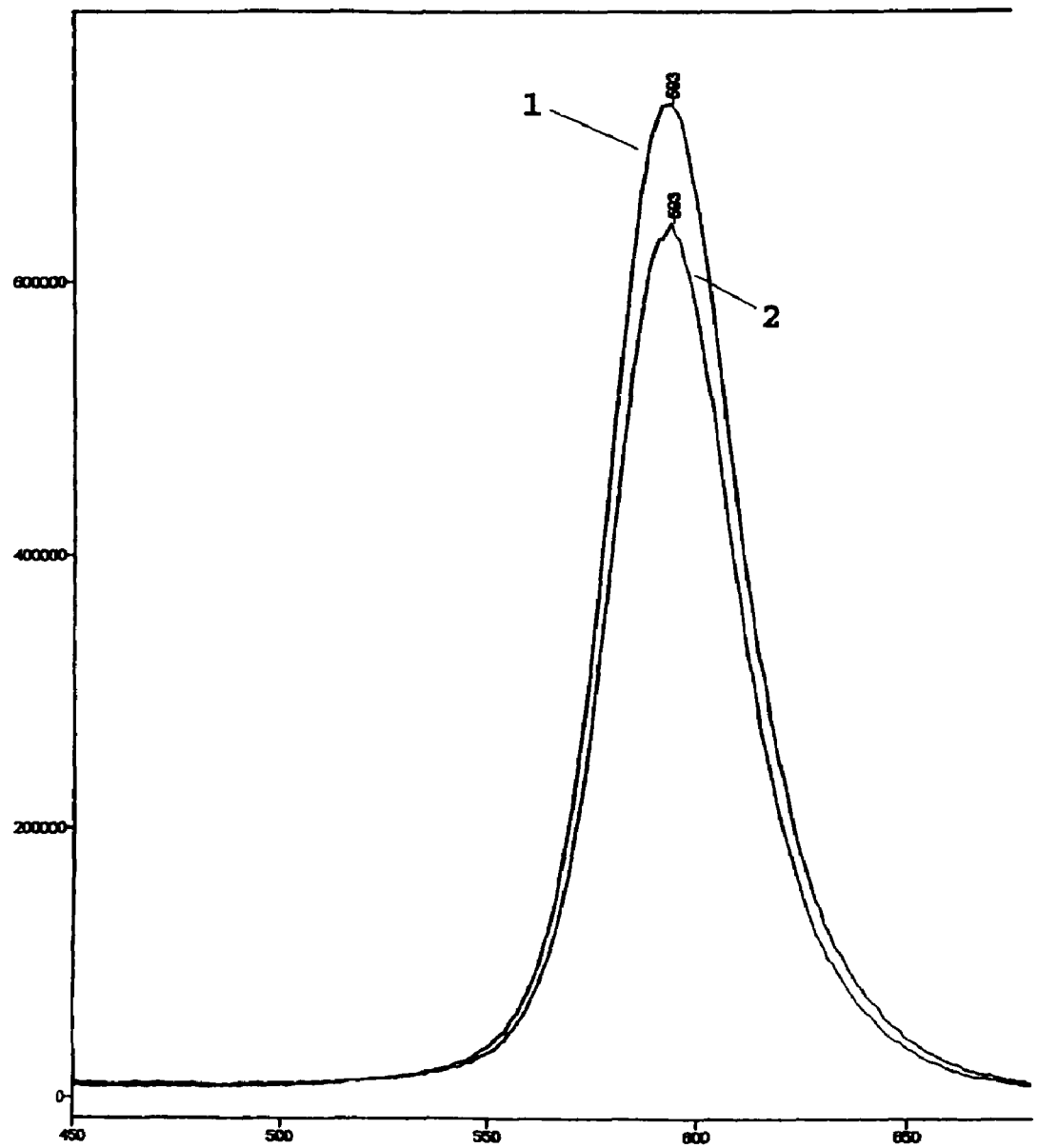
FIG. 3 is a graph showing an emission peak of one embodiment of functionalized, fluorescent nanocrystals (line A) as compared to an emission peak from another embodiment of functionalized, fluorescent nanocrystals.

The resultant functionalized, fluorescent nanocrystals were characterized by: stability in aqueous solutions of the general pH range of about 7 to about 10, with maximum stability in the range of from about pH 8 to about pH 10; availability of reactive functionalities on the surface of the functionalized, fluorescent nanocrystals (in this case, both amino groups and carboxyl groups) to which molecular probe may be operably bound; and an unexpected increase in fluorescence intensity. Referring to FIG. 3, compared is the fluorescence intensity emitted by functionalized, fluorescent nanocrystals coated with an imidazole-containing compound comprising histidine (FIG. 3, line 1; e.g., made by the process described in Example 2) with the fluorescence intensity emitted by functionalized, fluorescent nanocrystals coated with an imidazole containing compound comprising carnosine (FIG. 3, line 2), upon excitation at 410 nm. Based on its comparison with use of histidine as the imidazole-containing compound, using carnosine as the imidazole-containing compound in the coating process results in at least about 30 fold to as much as about 200 fold or more increase in fluorescence intensity, when compared to fluorescence intensity of either CdSe/ZnS fluorescent nanocrystals capped with a mercapto-based compound (e.g., mercaptoacetic acid) as known in the art, or CdSe/ZnS fluorescent nanocrystals (e.g., using comparable amounts, excitation conditions, and detection system as previously described herein). In another embodiment, these functionalized, fluorescent nanocrystals were further treated by cross-linking using the methods as previously described in Example 1 herein.

EXAMPLE 4

In one embodiment of a method of using the functionalized, fluorescent nanocrystals according to the present invention, it may be desirable to operably bind the functionalized, fluorescent nanocrystals to one or more molecules of molecular probe. Also provided by the present invention are compositions comprising functionalized, fluorescent nanocrystal operably bound to molecular probe. Such a composition may then be used in an assay to detect the presence or absence of a target molecule for which the molecular probe has binding specificity. As will be apparent to one skilled in the art, the reactive functionalities on the functionalized, fluorescent nanocrystals which are available for use in operably binding molecular probe will depend on the chemical nature (or species) of the imidazole-containing compound comprising the coat of the functionalized, fluorescent nanocrystals. For example, in using histidine or other imidazole-containing amino acid (other than histidine) as a component of the coating, one or more reactive functionalities (e.g., one or more amino acid side chains that may include, but is not limited to, free amino group, free carboxyl group, and a combination thereof) may be used to operably bind to one or more reactive functionalities of a molecular probe. As an illustrative example, a molecule of molecular probe having a free carboxyl-reactive group (e.g., amino group) may be operably bound to a free carboxyl group of a molecule of imidazole-containing compound comprising the coating of a functionalized, fluorescent nanocrystal using methods known in the art (e.g., treatment with EDC, followed by treatment with sulfo-NHS, as will be described herein in more detail). In an alternative example, a molecule of molecular probe having a free amino-reactive group (e.g., a carboxyl group) may be operably linked to a free amino group of a molecule of imidazole-containing compound comprising the coating of a functionalized, fluorescent nanocrystal using methods known in the art. If desirable, essentially the same procedure can be used to place a molecule comprising a spacer between the imidazole containing compound and the molecular probe in operably binding a functionalized, fluorescent nanocrystal to molecular probe. Such spacers are well known in the art and are commercially available (see, e.g., product catalog of Pierce Co.).

To illustrate this embodiment, molecular probe was operably linked to the functionalized, fluorescent nanocrystals using the methods summarized herein. In one illustrative example, functionalized, fluorescent nanocrystals were operably bound to streptavidin. Procedures similar to the following example for operably binding functionalized, fluorescent nanocrystals to streptavidin were also used to operably binding functionalized, fluorescent nanocrystals to molecular probe including, but not limited to, molecular probe selected from the group consisting of Con A, and IgG. In separate reactions, functionalized, fluorescent nanocrystals comprising a coating comprising histidine (produced by the methods described in Example 2 herein), and functionalized, fluorescent nanocrystals comprising a coating comprising carnosine, were operably bound to streptavidin. In these reactions, the carboxyl groups of streptavidin molecules were operably bound to the amino groups of functionalized, fluorescent nanocrystals. Streptavidin (e.g., 0.2 mg) was esterified by treatment with EDC (1-ethyl-3(3-dimethyl-aminopropyl]carbdimide) (e.g., 0.08 mg) and then reacted with sulfoNHS (sulfo-N-hydroxysuccinimide)hydroxysuccinimide) (e.g., 0.22 mg). The resulting solution was stirred at room temperature for 30 minutes. Mercaptoethanol was added to neutralize unreacted EDC at 20 mM concentration, followed by stirring for 15 minutes. The entire solution was then added dropwise, with stirring, to a buffered solution (e.g., 1 ml of 100 mM HEPES, 150 mM of NaCl, pH 7.5) containing the functionalized, fluorescent nanocrystals (e.g., about 1 mg); and the mixture was stirred for 2 hours at room temperature. Penicillamine (e.g., 100 mM) was added to quench the reaction; and the mixture was stirred for 30 minutes at room temperature or left overnight at 4° C. The resulting solution may then be used directly, or may be purified (e.g., using a gel filtration column).

In another illustrative example, functionalized, fluorescent nanocrystals were operably bound to streptavidin. In this reaction, 80 μl of a solution containing 1 mg/ml of sulfo-HSAB (N-hydroxysulfosuccinimidyl-4-azidobenzoate) in HEPES buffer was mixed with 300 μl of a streptavidin solution (6.6 mg/ml), and reacted for 1 hour at room temperature. Unreacted sulfo-HSAB was then removed by three rounds of centrifugal concentration, and then the final volume was adjusted to 500 μl with buffer. Of this final volume, 100 μl was mixed with 100 μl of functionalized, fluorescent nanocrystals (at approximately 10 mg solids/ml). The reaction mixture was incubated for 15 minutes at 37° C., and then was photoactivated by exposure to UV light of 265 nm for 15 minutes at room temperature.

A composition comprising functionalized, fluorescent nanocrystals operably bound to streptavidin was then tested in a detection system for the ability to bind a target molecule comprising biotinylated polystyrene microspheres (the beads being obtained commercially). In this assay, the biotinylated polystyrene microspheres served as target molecule. In this assay, 50 μl of a composition comprising functionalized, fluorescent nanocrystals operably bound to streptavidin (e.g., about 1 mg) was contacted with (using gently mixing and an incubation at room temperature for 1 hour) 50 μl of a solution comprising the biotinylated polystyrene microspheres (e.g., about a 2.5% solution. The microspheres were then washed three times with buffer and repeated centrifugation for pelleting the microspheres. The final volume was adjusted with buffer to 200 μl, and a drop was placed and mounted on a glass slide. Examination of a preparation of biotinylated polystyrene microspheres alone and of biotinylated polystyrene microspheres reacted with functionalized fluorescent nanocrystals operably bound to streptavidin was performed under a fluorescence microscope using a 100× objective operatively linked to a CCD camera as a detection system, and with excitation at 300 nm. Target molecules comprising biotinylated polystyrene microspheres were fluorescent because of functionalized, fluorescent nanocrystals bound thereto, indicating successful operably binding of the biotinylated microspheres to the composition comprising functionalized, fluorescent nanocrystals operably bound to streptavidin.

As apparent to one skilled in the art from the descriptions herein, in using the functionalized, fluorescent nanocrystals according to the present invention, the functionalized, fluorescent nanocrystals (with or without molecular probe, depending on the assay) are excited with an excitation wavelength, and then detected by appropriate detection means or system (e.g., one or more of: photodetector, filter, charge couple device camera (CCD camera), fluorescence microscope, spectrofluorimeter, endoscopic imaging system, endoscopic fluorescence imaging microscope, a fiber optic fluorescence imaging microscope, a fluorescence cube, a computer for digitalizing a fluorescence image, and the like). In a preferred embodiment, the appropriate detection means can detect fluorescence peaks in the spectral range of about 400 nm to about 800 nm; and, when multicolor fluorescence is desired to be detected in the detection system, distinguish between discrete fluorescence peaks within that range. Quantitation of the amount of functionalized, fluorescent nanocrystals present in a detection system is directly related to the intensity of an emitted fluorescence peak (e.g., as measured by number of events of fluorescence versus the intensity of fluorescence, using a fluorescence microscope with a video camera attachment and computer software program for manipulating and storing the data collected). As apparent to one skilled in the art of nanocrystals, the absorbance peak and fluorescence peak emissions depend on properties of the nanocrystals which may include, but are not limited to: the chemical nature of the fluorescent nanocrystal; doping agent (if any) of the fluorescent nanocrystal; core size of the fluorescent nanocrystal; and as described here, the nature of the coating comprising the imidazole-containing compound.

EXAMPLE 5

This example illustrates embodiments of a process of making the functionalized, fluorescent nanocrystals according to the present invention. For this and subsequent examples, semiconductor nanocrystals comprising core nanocrystals were produced using a continuous flow process as described in the U.S. Pat. No. 6,179,912. The following parameters were used to produce nanocrystals of cadmium selenide (CdSe): 10 g TOPO; 18.9 μl of Me$_2$Cd (dimethyl cadmium; e.g., 2.63×10$^{-4}$ moles of Cd); 198.9 μl of TOPSe (1M solution of Se in TOP; e.g., 1.989×10$^{-4}$ moles of Se); 4.5 ml of TOP; nucleation temperature ($T_n$) of 300° C.; growth temperature ($T_g$) of 280° C.; and flow rate of 0.1 ml/min. The resulting CdSe nanocrystals displayed fluorescence at a wavelength of 578 nm, with an excitation wavelength of 410 nm, and a narrow bandwidth at half height of about 29 nm.

Figure 4:
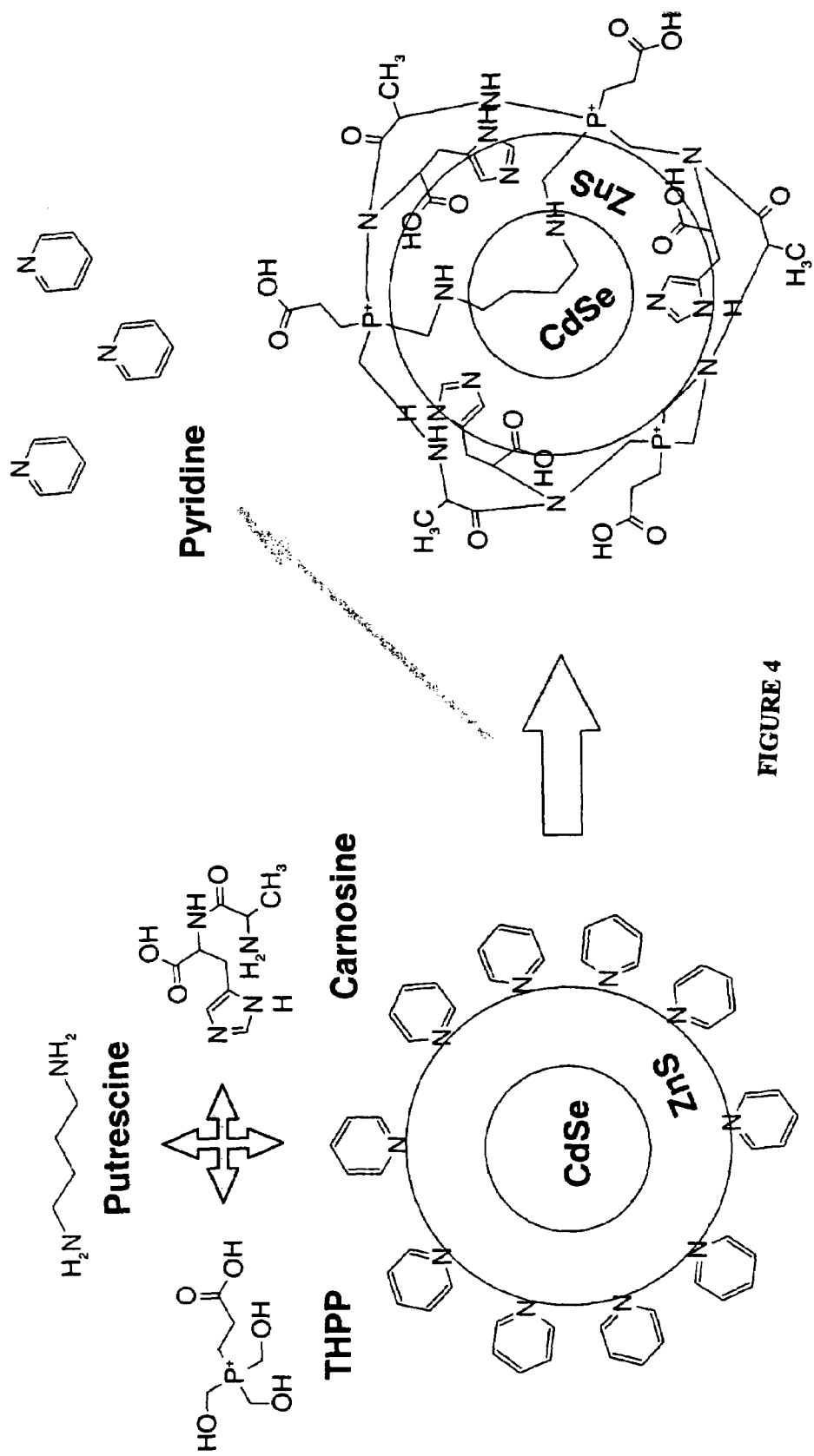
FIG. 4 is a schematic representation of several embodiments of the functionalized, fluorescent nanocrystals, and a process for their formation.
Figure 5:
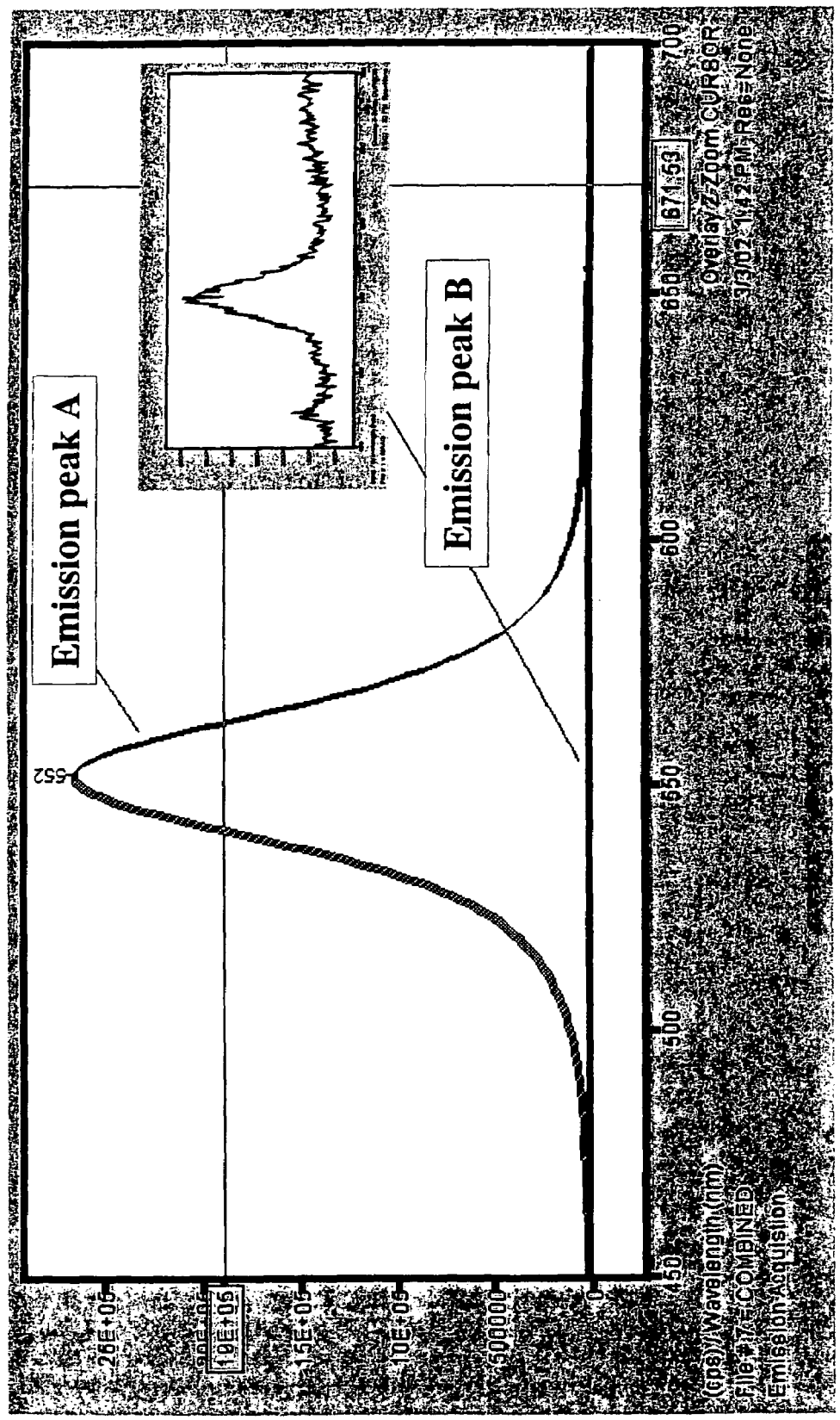
FIG. 5 is a graph showing a comparison of emission peak of fluorescent nanocrystals using a mercapto-based method ("Peak B") and emission peak of functionalized, fluorescent nanocrystals ("Peak A").

FIG. 4 shows a general scheme for making the functionalized, fluorescent nanocrystals according to the present invention. In one embodiment, the process of making functionalized, fluorescent nanocrystals comprises: contacting the fluorescent nanocrystals comprising a combined semiconductor (e.g., CdSe, ZnS or the like) with a solution comprising an (one or more) imidazole-containing compound and then with a solution comprising a (one or more) phosphine cross-linking compound; wherein imidazole-containing compound operably binds to the metal cation (e.g., Cd++, Zn++ or the like) and the phosphine cross-linking compound (e.g., alkyl phosphine compound) operably binds to the counterpart non metal element (e.g., S, Se, or the like) in producing a coat over the fluorescent nanocrystals in forming functionalized, fluorescent nanocrystals.

As previously described herein in more detail, the fluorescent nanocrystals which are coated by the process may comprise core semiconductor nanocrystals, core/shell semiconductor nanocrystals, doped metal oxide nanocrystals, or a combination thereof. With respect to metal cations, imidazole-containing compounds have been reported to operably bind metal ions which may include, but arc not limited to one or more of, $Zn^{2+}$ $Cu^{2+}$$Fe^{2+}$, $Ni^{2+}$, $Cd^{2+}$, $Co^{2+}$, and the like. With respect to non metal counter part anions, a phosphine cross-linking compound is capable of operably binding to non metal elements which may include, but are not limited to one or more of, O, S, Se, Te, PO and the like; and depending on the phosphine cross-linking compound chosen (e.g., phosphine oxide or a phosphonium), may further be capable of binding to metal ions such as Zn, Cd, and the like.

For example, core nanocrystals were coated to produce the functionalized, fluorescent nanocrystals according to the present invention. In one embodiment, the core nanocrystals were coated by a mixture which comprised an imidazole-containing compound and an alkyl phosphine-containing cross-linker. As a general guideline, the coating process may comprise inclusion of components comprising, per 0.5 milligram of core fluorescent nanocrystals: imidazole-containing compound in an amount ranging from about 0.25 mmole to about 2.5 mmole; alkyl phosphine-containing cross-linker in an amount ranging from about 0.25 mmole to about 2.5 mmole; and a polyamine in an amount ranging from about 0 mmole to about 2.5 mmole. As apparent to one skilled in the art, the amount of each individual component may vary depending on the particular imidazole-containing compound used, the alkyl phosphine-containing compound used, the nature (e.g., chemical composition) of fluorescent nanocrystals to be functionalized, the nature of the surface of the fluorescent nanocrystals to be coated, the ratio of other components in the coating process, and the pH of the buffer system used in the coating process. For example, prepared was a 30 mM carnosine (imidazole containing compound) solution in a 1 M CAPSO buffer (3-(Cyclohexylamino)-2-hydroxy-1-propanesulfonic acid, sodium salt, pH 9.6). Other suitable buffers known in the art which provide buffering in a range of from about pH 8.0 to about pH 11, may be used in place of the CAPSO buffer (e.g., a sodium carbonate buffer, TAPS buffer (N-tris(hydroxymethyl)methyl-aminopropanesulfonic acid), and the like). To 10 ml of the carnosine solution was added 0.5 to 3 mg of CdSe nanocrystals (core crystals) suspended in a minimal volume (e.g., from about 60 µl to about 200 µl) of organic solvent (e.g., chloroform or pyridine). After mixing, and incubation for about 1 hr at room temperature, also was added 1.2 ml of 60 mM THPP (beta-[Tris(hydroxymethyl)phosphino]propionic acid, alkyl phosphine-containing cross-linker). After one hour of gentle mixing, 100 µl of 1 M putrescine (polyamine) was added and mixed for additional hour. The cycle of the addition of THPP and putrescine was repeated three to four times. The final solution was treated with formaldehyde at 100 mM final concentration for about 1 hour period. The functionalized, fluorescent nanocrystals were then purified by a process selected from the group consisting of: size exclusion chromatography, dialysis, centrifugation, and a combination thereof. For example the solution comprising functionalized, fluorescent nanocrystals was dialyzed against a suitable buffer such like PBS (phosphate buffered saline) using 3000 Dalton (D) molecular weight cutoff (MCO) dialysis membranes. This process for making the functionalized, fluorescent nanocrystals was repeated, whereby the relative amounts of each component were varied. From these formulation studies, a preferred ratio of components that showed optimal properties of fluorescence and stability (in an aqueous environment and at a wide pH range) comprises: 0.5 to 1 mg of core nanocrystals (e.g., CdSe); 0.3 mmole carnosine; 0.15 mmole THPP; 0.15 mmole putrescine, and 1 mmole formaldehyde. The resultant functionalized, fluorescent nanocrystals were characterized by: stability in aqueous solutions of the general pH range of about 6 to about 10, with optimal stability in the range of from about pH 7 to about pH 9; available reactive functionalities on the surface of the functionalized, fluorescent nanocrystals (in this case, carboxyl groups) to which molecular probe may be operably bound; and an enhancement of fluorescence intensity of between about 10 to 100 fold when compared to fluorescence intensity of fluorescent nanocrystals in organic solvent. The comparison of fluorescence intensity was made with an equivalent amount of fluorescent nanocrystals made using core nanocrystals from the same run in the continuous flow process as the core nanocrystals coated with the process according to the present invention; excitation with the same excitation light source (e.g., 410 nm); and detection using the same detection system. The detection system used was a standard spectrofluorometer, wherein the instrument's software calculated the area under the acquired emission peak as a measurement of fluorescence intensity, as standard in the art. With respect to measurement of stability, less than optimal stability was characterized by one or more of a tendency for the functionalized, fluorescent nanocrystals to aggregate over time when present in an aqueous solution, or a loss of fluorescence intensity (e.g., loss of the observed enhancement or loss of any detectable emission at all) associated with functionalized, fluorescent nanocrystals.

EXAMPLE 6

In another embodiment, fluorescent nanocrystals comprising core/shell nanocrystals are coated by a coating solution comprising imidazole-containing compound and then with a solution comprising alkyl phosphine-containing compound; wherein imidazole-containing compound operably binds to the metal cation (e.g., Cd++, Zn++ or the like) and the alkyl phosphine-containing compound operably binds to the counterpart non metal element (e.g., S, Se, or the like) in producing a coat over the fluorescent nanocrystals in forming functionalized, fluorescent nanocrystals. As a general guideline, the core/shell nanocrystals coating process may comprise inclusion of components comprising, per milligram of fluorescent nanocrystals: imidazole-containing compound in an amount ranging from about 0.25 mmole to about 2.5 mmole; alkyl phosphine-containing cross-linker in an amount ranging from about 0.25 mmole to about 2.5 mmole; and a polyamine in an amount ranging from about 0 mmole to about 2.5 mmole. As apparent to one skilled in the art, the amount of each individual component may vary depending on the particular imidazole-containing compound used, the alkyl phosphine-containing compound used; the nature (e.g., chemical composition) of fluorescent nanocrystals to be functionalized, the nature of the surface of the fluorescent nanocrystals to be coated, the ratio of other components in the coating process, and the pH of the buffer system used in the coating process. For example, prepared was a 30 mM carnosine (imidazole containing compound) solution in a 1 M CAPSO buffer (3-(Cyclohexylamino)-hydroxy-propanesulfonic acid, sodium salt, pH 9.6). Other suitable buffers known in the art which provide buffering in a range of from about pH 8.0 to about pH 11, may be used in place of the CAPSO buffer (e.g., a sodium carbonate buffer, TAPS buffer (N-tris(hydroxymethyl)methyl-aminopropanesulfonic acid), and the like). To 10 ml of the carnosine solution was added 0.5 to 3 mg of CdSe nanocrystals (core crystals) suspended in a minimal volume (e.g., from about 60 µl to about 200 µl) of organic solvent (e.g., chloroform or pyridine). After mixing, and incubation for about 1 hr at room temperature, also was added 1.2 ml of 60 mM THPP (beta-[Tris(hydroxymethyl)phosphino]propionic acid, alkyl phosphine-containing cross-linker). After one hour of gentle mixing, 100 µl of 1 M putrescine (polyamine) was added and mixed for additional hour. The cycle of the addition of THPP and putrescine was repeated three to four times. The final solution was treated with formaldehyde at 100 mm final concentration for about 1 hour period. The functionalized, fluorescent nanocrystals were then purified by a process selected from the group consisting of: size exclusion chromatography, dialysis, centrifugation, and a combination thereof. For example the solution comprising functionalized, fluorescent nanocrystals was dialyzed against a suitable buffer such like PBS (phosphate buffered saline) using 3000 D MCO dialysis membranes. This process for making the functionalized, fluorescent nanocrystals was repeated, whereby the relative amounts of each component were varied. From these formulation studies, a preferred ratio of components that showed optimal properties of fluorescence and stability (in an aqueous environment and at a wide pH range) comprises: 1 to 2 mg of core/shell nanocrystals (e.g., CdSe/ZnS); 0.3 mmole carnosine; 0.15 mmole THPP; 0.15 mmole putrescine, and 1 mmole formaldehyde. The resultant functionalized, fluorescent nanocrystals were characterized by: stability in aqueous solutions of the general pH range of about 6 to about 10, with optimal stability in the range of from about pH 7 to about pH 9; available reactive functionalities on the surface of the functionalized, fluorescent nanocrystals (in this case, carboxyl groups) to which molecular probe may be operably bound; and an unexpected enhancement of fluorescence intensity comprising at least 50 fold to as much as about 1100 fold or more (see, e.g., FIG. 5 and inset of FIG. 5), when compared to fluorescence intensity of functionalized fluorescent nanocrystals known in the art (e.g., CdX/YZ fluorescent nanocrystals in organic solvent or CdX/YZ fluorescent nanocrystals capped with mercapto-based compound) (see, e.g., FIG. 5). The comparison of fluorescence intensity was made with an equivalent amount of fluorescent nanocrystals, made using core/shell nanocrystals from the same preparation; excitation with the same excitation light source (e.g., 410 nm); and detection using the same detection system. Thus, in accordance with the present invention, the process of coating results in, and resultant functionalized, fluorescent nanocrystals comprise, a coating that provides at least a 50 fold increase in fluorescence intensity than comparable fluorescent nanocrystals known in the art (e.g., CdX/YZ fluorescent nanocrystals in organic solvent or CdX/YZ fluorescent nanocrystals capped with mercapto-based compound) (see, e.g., FIG. 5). Such an increase is an unexpected result with respect to the degree of enhancement of fluorescence intensity. In a more preferred embodiment of the present invention, the process of coating results in, and resultant functionalized, fluorescent nanocrystals comprise, a coating that provides at least about 1100 fold increase in fluorescence intensity than comparable fluorescent nanocrystals known in the art (e.g., CdX/YZ fluorescent nanocrystals in organic solvent or CdX/YZ fluorescent nanocrystals capped with mercapto-based compound). Such an increase is an unexpected result with respect to the degree of enhancement of fluorescence intensity.

EXAMPLE 7

In this example, provided is another embodiment of process of making functionalized, fluorescent nanocrystals by coating fluorescent nanocrystals with a coating comprising histidine as an imidazole-containing compound. As a general guideline, the core/shell nanocrystals coating process may comprise inclusion of components comprising, per milligram of fluorescent nanocrystals: imidazole-containing compound in an amount ranging from about 0.25 mmole to about 2.5 mmole; alkyl phosphine-containing cross-linker in an amount ranging from about 0.25 mmole to about 2.5 mmole; and a polyamine in an amount ranging from about 0 mmole to about 2.5 mmole. As apparent to one skilled in the art, the amount of each individual component may vary depending on the particular imidazole-containing compound used, the alkyl phosphine-containing compound used, the nature (e.g., chemical composition) of fluorescent nanocrystals to be functionalized, the nature of the surface of the fluorescent nanocrystals to be coated, the ratio of other components in the coating process, and the pH of the buffer system used in the coating process.

For example, prepared was a 30 mM carnosine (imidazole containing compound) solution in a 1 M CAPSO buffer (3-(Cyclohexylamino)-hydroxy-propanesulfonic acid, sodium salt, pH 9.6). Other suitable buffers known in the art as previously described herein. To 10 ml of the carnosine solution was added 0.5 to 3 mg of CdSe nanocrystals (core crystals) suspended in a minimal volume (e.g., from about 60 µl to about 200 µl) of organic solvent (e.g., chloroform or pyridine). After mixing, and incubation for about 1 hr at room temperature, also was added 1.2 ml of 60 mM THPP (beta[Tris(hydroxymethyl)phosphino)propioninc acid, alkyl phosphine-containing cross-linker). After one hour of gentle mixing, 100 µl of 1M putrescine (polyamine) was added and mixed for additional hour. The cycle of the addition of THPP and putrescine was repeated three to four times. The final solution was treated with formaldehyde at 100 mM final concentration for about 1 hour period. The functionalized, fluorescent nanocrystals were then purified as previously described herein. This process for making the functionalized, fluorescent nanocrystals was repeated, whereby the relative amounts of each component were varied. From these formulation studies, a preferred ratio of components that showed optimal properties of fluorescence and stability (in an aqueous environment and at a wide pH range) comprises: 1 to 2 mg of core/shell nanocrystals (e.g., CdSe/ZnS); 0.3 mmole carnosine; 0.15 mmole THPP; 0.15 mmole putrescine, and 1 mmole formaldehyde.

The resultant functionalized, fluorescent nanocrystals were characterized by: stability in aqueous solutions of the general pH range of about 6 to about 10, with optimal stability in the range of from about pH 7 to about pH 9; availability of reactive functionalities on the surface of the functionalized, fluorescent nanocrystals (in this case, carboxyl groups) to which molecular probe may be operably bound; and an unexpected enhancement of fluorescence intensity comprising at least 50 fold to as much as about 1100 fold or more, when compared to fluorescence intensity of functionalized fluorescent nanocrystals known in the art (e.g., CdX/YZ fluorescent nanocrystals in organic solvent or CdX/YZ fluorescent nanocrystals capped with mercapto-based compound). The comparison of fluorescence intensity was made as previously described herein.

EXAMPLE 8

In one embodiment of a method of using the functionalized, fluorescent nanocrystals according to the present invention, it may be desirable to operably bind the functionalized, fluorescent nanocrystals to one or more molecules of molecular probes. Also provided by the present invention are compositions comprising functionalized, fluorescent nanocrystals operably bound to molecular probe. Such a composition may then be used in an assay to detect the presence or absence of a target molecule for which the molecular probe has binding specificity. As will be apparent to one skilled in the art, the reactive functionalities on the functionalized, fluorescent nanocrystals which are available for use in operably binding molecular probe will depend on the chemical nature (or species) of the one or more imidazole-containing compounds and the one or more phosphine cross-linking compounds comprising the coat of the functionalized, fluorescent nanocrystals. For example, in using carnosine or other imidazole-containing compounds (other than carnosine) and THPP or other phosphine cross-linking compounds as components of the coating, one or more reactive functionalities (e.g., free carboxyl group, amino group, and a combination thereof) may be used to operably bind to one or more reactive functionalities of a molecular probe. As an illustrative example, a molecule of molecular probe having a free carboxyl-reactive group of a molecule of alkyl phosphine or an imidazole-containing compound comprising the coating of a functionalized, fluorescent nanocrystal using methods known in the art (e.g., treatment with EDC, followed by treatment with sulfo-NHS, as will be described herein in more detail). In an alternative example, a molecule of molecular probe having a free amino-reactive group (e.g., a carboxyl group) may be operably linked to a free amino group of a molecule of an imidazole-containing compound or phosphine cross-linking compound comprising the coating of a functionalized, fluorescent nanocrystal using methods known in the art. If desirable, essentially the same procedure can be used to place a molecule comprising a spacer arm between the imidazole-containing compound and phosphine cross-linking compound on one side and the molecular probe in operably binding a functionalized, fluorescent nanocrystal to molecular probe. Such spacers are well known in the art and are commercially available (see, e.g., product catalog of Pierce Co.).

To illustrate this embodiment, molecular probe was operably linked to the functionalized, fluorescent nanocrystals using the method summarized herein. In one illustrative example, functionalized, fluorescent nanocrystals were operably bound to avidin. Procedures similar to the following example for operably binding functionalized, fluorescent nanocrystals to avidin were also used to operably binding functionalized, fluorescent nanocrystals to molecular probe including, but not limited to, molecular probe selected from the group consisting of ConA, lectin, and IgG. In separate reactions, functionalized, fluorescent nanocrystals comprising a coating comprising THPP and carnosine (produced by the methods described in Example 6 herein), were operably bound to avidin. In these reactions, the amino groups of avidin were operably bound to the carboxyl groups of functionalized, fluorescent nanocrystals. Two ml of 100 ug/ml functionalized, fluorescent nanocrystals in MES buffer (MES 50 mM, NaCl 250 mM, pH6.5) were esterified by treatment with 5 mM EDC (1-ethyl-3-[3-dimethyl-aminopropyl]carbdiimide) and 10 mM sulfo-NHS (sulfo-N-hydroxysuccinimide). The resulting solution was mixed at room temperature for 15 minutes, and then was dialyzed against the MES buffer (described above) for 90 minutes using dialysis membrane with a MWCO of 3000 D. To the resulting solution then was added 100 µg avidin (dissolved in 100 µl PBS), and the entire solution was mixed at room temperature for 30 minutes. Then, the reaction was terminated by adding 25 mM glycine and mixing for another 30 minutes. The solution was then purified from excess nanocrystals and reagents using ultrafiltration centrifugal membranes with a MWCO of 50 KD.

A composition comprising functionalized, fluorescent nanocrystals operably bound to avidin was then evaluated using three different assays:

A. The Binding Ability of a Target Molecule Comprising Biotinylated Polystyrene Microspheres (the Beads Being Obtained Commercially)

Figure 6A:
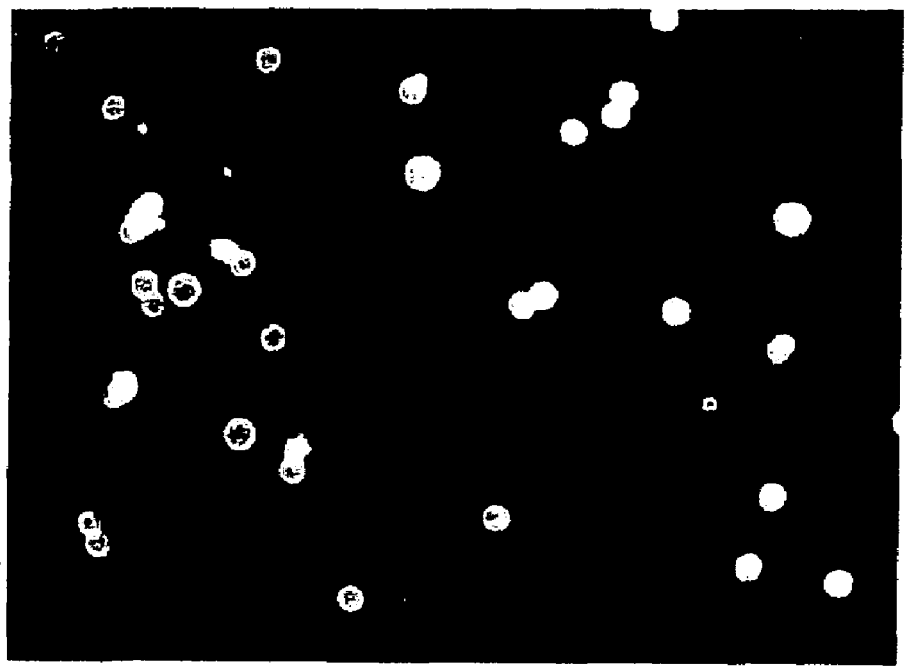
FIG. 6A is an image showing, after exposure to an excitation light source, biotinylated polystyrene microspheres treated with avidin covalently conjugated to the functionalized, fluorescent nanocrystals.
Figure 6B:
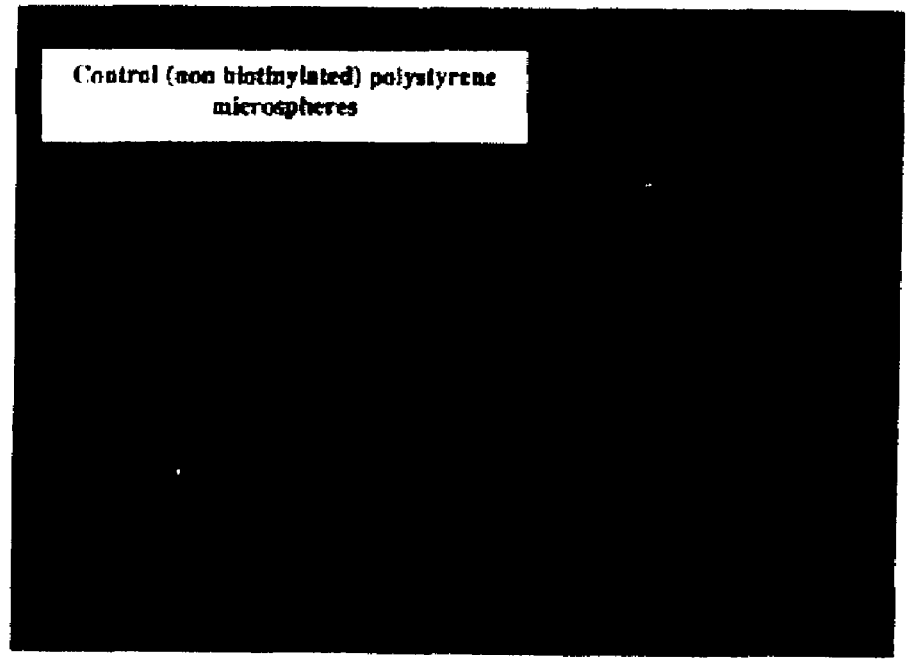
FIG. 6B is an image showing, after exposure to an excitation light source, non-biotinylated polystyrene microspheres treated with avidin covalently conjugated to the functionalized, fluorescent nanocrystals.

In this assay, the biotinylated polystyrene microspheres served as target molecule. In this assay, 100 µl of a composition comprising functionalized, fluorescent nanocrystals operably bound to avidin (described above) was contacted with 50µ of 1% suspension comprising biotinylated polystyrene microspheres for 15 minutes. The microspheres were then washed three times with buffer and repeated centrifugation. The final volume was adjusted with PBS to 100 µl, and a drop was mounted on a glass slide. Examination of a preparation of biotinylated polystyrene microspheres, and of non biotinylated polystyrene microspheres (control) was performed under fluorescence microscope using 200× objective linked to a CCD camera as a detection system, and with excitation at ~300 nm. As shown in FIGS. 6A and 6B, only the target molecules comprising biotinylated polystyrene microspheres were successfully operably bound to the composition comprising functionalized, fluorescent nanocrystals operably bound to avidin.

B. Assay for Resistance to Photobleaching

Biotinylated microspheres stained with functionalized, fluorescent nanocrystals operably bound to avidin as mentioned above were exposed to a direct UV light (excitation ~300 nm) over a period from 0 to 65 minutes. As shown in FIGS. 7A and 7B, the staining of the biotinylated microspheres by functionalized, fluorescent nanocrystals operably bound to avidin was stable and did not photobleach over the period of exposure.

C. Detection of Target Molecule

Paraffin-embedded liver microscopic sections were treated with primary biotinylated antibodies against mouse IgG using methods well known in the art, and then were stained for about 90 minutes with a solution of avidinylated fluorescent nanocrystals functionalized according to the method of the present invention (5 µg/ml avidin conjugated nanocrystals in PBS). After a brief washing with PBS, the slides were examined under fluorescence microscope using 200× objective linked to a CCD camera as a detection system, and with excitation at ~300 nm. As shown in FIGS. 8A and 8B, the target molecules comprising biotinylated antibodies against mouse IgG were successfully operably bound to the composition comprising functionalized, fluorescent nanocrystals operably bound to avidin.

As apparent to one skilled in the art from the descriptions herein, appropriate detection systems are well known in the art; e.g., any detection system that can detect fluorescent peaks in a general spectral range of from about 400 nm to about 800 nm, and preferably may further distinguish between discrete fluorescence peaks within that range in analysis involving multicolor fluorescence. Quantitation of the amount of functionalized fluorescent nanocrystals detected by a detection system is directly related to the intensity of the emitted fluorescence (e.g., as measured by number of events of fluorescence versus the intensity of fluorescence). As apparent to one skilled in the art, the absorbance peak and fluorescence peak emission, of a functionalized fluorescent nanocrystal according to the present invention will depend on the composition of the core nanocrystal, the composition of the coatings used, and the like.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the present invention.

I claim:

1. A functionalized fluorescent nanocrystal comprised of:
 a fluorescent nanocrystal; and
 an imidazole-containing capping layer wherein the capping layer further comprises a phosphine cross-linking compound.

2. The functionalized fluorescent nanocrystal of claim 1, wherein the fluorescent nanocrystal comprises a core semiconductor nanocrystal, a core/shell semiconductor nanocrystal, a doped metal oxide nanocrystal, or a mixture thereof.

3. The functionalized fluorescent nanocrystal of claim 2, wherein the fluorescent nanocrystal is a core nanocrystal co-precipitated with a metal salt shell.

4. The functionalized fluorescent nanocrystal of claim 3, wherein the metal salt shell comprises a semiconductor material with a higher band gap energy than the core nanocrystal.

5. The functionalized fluorescent nanocrystal of claim 3, wherein the core nanocrystal comprises a Group II-VI semiconductor and the metal salt shell comprises a Group II-VI semiconductor.

6. The functionalized fluorescent nanocrystal of claim 3, wherein the core nanocrystal comprises a Group II-VI semiconductor and the metal salt shell comprises a compound comprising sulfur and a metal selected from the group consisting of zinc, copper, iron, nickel, cadmium, cobalt, and mixtures thereof.

7. The functionalized fluorescent nanocrystal of claim 3, wherein the core nanocrystal comprises cadmium selenide and the metal salt shell comprises zinc sulfide.

8. The functionalized fluorescent nanocrystal of claim 3, wherein the imidazole-containing capping layer comprises a functional group comprising an ion operably bound to the metal salt shell.

9. The functionalized fluorescent nanocrystal of claim 3, wherein the imidazole-containing capping layer comprises a nitrogen operably bound to the metal salt shell.

10. The functionalized fluorescent nanocrystal of claim 3, wherein the capping layer is uniformly deposited over an outer surface of the fluorescent nanocrystal.

11. The functionalized fluorescent nanocrystal of claim 3, wherein the imidazole-containing capping layer passivates the fluorescent nanocrystal.

12. The functionalized fluorescent nanocrystal of claim 3, wherein the fluorescence intensity of the functionalized fluorescent nanocrystal is greater than the fluorescence intensity of a non-functionalized fluorescent nanocrystal.

13. The functionalized fluorescent nanocrystal of claim 3, wherein the fluorescence intensity of the functionalized fluorescent nanocrystal is enhanced up to about 1100 fold when compared to a non-functionalized fluorescent nanocrystal.

14. The functionalized fluorescent nanocrystal of claim 3, wherein the fluorescence intensity of the functionalized fluorescent nanocrystal is enhanced about 30 to about 300 fold when compared to a non-functionalized fluorescent nanocrystal.

15. The functionalized fluorescent nanocrystal of claim 3, wherein the fluorescence intensity of the functionalized fluorescent nanocrystal is enhanced about 10 to about 100 fold when compared to a non-functionalized fluorescent nanocrystal.

16. The functionalized fluorescent nanocrystal of claim 3, wherein the imidazole-containing capping layer is cross-linked.

17. The functionalized fluorescent nanocrystal of claim 3, wherein the functionalized fluorescent nanocrystal is soluble in aqueous solutions.

18. The functionalized fluorescent nanocrystal of claim 3, wherein the functionalized fluorescent nanocrystal is stable in aqueous solutions at about pH 6 to about pH 10.5.

19. The functionalized fluorescent nanocrystal of claim 3, wherein the functionalized fluorescent nanocrystal is stable in aqueous solutions at about pH 7 to about pH 9.

20. The functionalized fluorescent nanocrystal of claim 3, wherein the functionalized fluorescent nanocrystal is stable in aqueous solutions at about pH 8 to about pH 10.

21. The functionalized fluorescent nanocrystal of claim 3, wherein the functionalized fluorescent nanocrystal is operably bound to a molecular probe.

22. A method for detecting a target molecule, the method comprising:
    forming a complex by operably bonding a functionalized fluorescent nanocrystal to a target molecule, wherein the functionalized fluorescent nanocrystal comprises an imidazole-containing capping layer wherein the capping layer further comprises a phosphine cross-linking compound;
    exciting the complex; and
    detecting light emitted from the complex.

* * * * *